United States Patent
Robinson et al.

(10) Patent No.: US 12,383,748 B2
(45) Date of Patent: Aug. 12, 2025

(54) SYSTEMS AND METHODS FOR WIRELESS COMMUNICATION WITH IMPLANTABLE DEVICES

(71) Applicant: William Marsh Rice University, Houston, TX (US)

(72) Inventors: Jacob Robinson, Houston, TX (US); Fatima Alrashdan, Houston, TX (US); Kaiyuan Yang, Houston, TX (US); Zhanghao Yu, Houston, TX (US); Joshua Woods, Houston, TX (US); Amanda Singer, Houston, TX (US); Matthew Parker, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 18/914,037

(22) Filed: Oct. 11, 2024

(65) Prior Publication Data

US 2025/0032804 A1    Jan. 30, 2025

Related U.S. Application Data

(62) Division of application No. 18/336,787, filed on Jun. 16, 2023.

(60) Provisional application No. 63/353,371, filed on Jun. 17, 2022.

(51) Int. Cl.
*A61N 1/372* (2006.01)
*A61N 1/05* (2006.01)
*A61N 1/36* (2006.01)
*A61N 1/378* (2006.01)

(52) U.S. Cl.
CPC ..... *A61N 1/37223* (2013.01); *A61N 1/36062* (2017.08); *A61N 1/3727* (2013.01); *A61N 1/37288* (2013.01); *A61N 1/3787* (2013.01)

(58) Field of Classification Search
CPC ............ A61N 1/37223; A61N 1/36062; A61N 1/3727; A61N 1/37288; A61N 1/3787; A61N 1/0534
See application file for complete search history.

(56) References Cited

U.S. PATENT DOCUMENTS

| | | |
|---|---|---|
| 2007/0252593 A1 | 11/2007 | Takeuchi et al. |
| 2007/0282378 A1 | 12/2007 | Huang et al. |
| 2010/0015918 A1 | 1/2010 | Liu et al. |

(Continued)

FOREIGN PATENT DOCUMENTS

| | | | |
|---|---|---|---|
| WO | WO 2020-206332 | 10/2020 | |
| WO | WO-2020206332 A1 * | 10/2020 | ......... A61N 1/37223 |

OTHER PUBLICATIONS

Ghanbari et al., "A Sub-mm3 Ultrasonic Free-Floating Implant for Multi-Mote Neural Recording," JSSC, Nov. 2019.

(Continued)

*Primary Examiner* — Brian T Gedeon
(74) *Attorney, Agent, or Firm* — Parker Highlander PLLC

(57) ABSTRACT

Exemplary embodiments of this disclosure include apparatus, systems and methods utilizing a passive, power-efficient backscattering communication system that enables transmitting data wirelessly between implantable magnetoelectric (ME) devices and an external base station. Certain embodiments encode the transmitted data through modulating the resonance frequency of a ME film by digitally tuning its electric loading conditions.

19 Claims, 41 Drawing Sheets

(56) References Cited

U.S. PATENT DOCUMENTS

| | | | |
|---|---|---|---|
| 2010/0274305 A1 | 10/2010 | Gliner et al. | |
| 2011/0276111 A1* | 11/2011 | Carbunaru | A61N 1/37229 607/61 |
| 2014/0358024 A1* | 12/2014 | Nelson | A61N 1/36139 607/45 |
| 2019/0150883 A1 | 5/2019 | Maharbiz et al. | |
| 2021/0401351 A1 | 12/2021 | Choi et al. | |
| 2022/0168579 A1 | 6/2022 | Robinson et al. | |
| 2023/0248980 A1 | 8/2023 | Willis et al. | |

OTHER PUBLICATIONS

Jia et al., "A mm-sized free-floating wirelessly powered implantable optical stimulating system-on-a-chip," IEEE International Solid-State Circuits Conference—(ISSCC), San Francisco, CA, USA, pp. 468-470, Feb. 2018.

Khalifa et al., "The Microbead: A Highly Miniaturized Wirelessly Powered Implantable Neural Stimulating System," *IEEE Transactions on Biomedical Circuits and Systems*, 12(3):521-531, Jun. 2018.

Kuo et al., "Inductive Wireless Power Transfer and Uplink Design for a CMOS Tag With 0.01 mm2 Coil Size," IEEE Microwave and Wireless Components Letters, 26(10):852-854, Oct. 2016.

Leung et al., "Distributed Microscale Brain Implants with Wireless Power Transfer and Mbps Bi-directional Networked Communications," IEEE Custom Integrated Circuits Conference (CICC), Austin, TX, USA, pp. 1-4, Apr. 2019.

Li et al., "A 13.56 MHz Wireless Power Transfer System With Reconfigurable Resonant Regulating Rectifier and Wireless Power Control for Implantable Medical Devices," in IEEE Journal of Solid-State Circuits, 50(4):978-989, Apr. 2015.

Lim et al., "A Light Tolerant Neural Recording IC for Near-Infrared-Powered Free Floating Motes," *Symp VLSI Circuits*, Jun. 2021.

Office Action issued in U.S. Appl. No. 18/336,787, mailed Jan. 30, 2024.

Office Action issued in U.S. Appl. No. 18/336,787, mailed Nov. 7, 2023.

Pan et al., "An inductively-coupled wireless power-transfer system that is immune to distance and load variations," IEEE International Solid-State Circuits Conference (ISSCC), San Francisco, CA, USA, pp. 382-383, Feb. 2017.

Park et al., "A Frequency-Splitting-Based Wireless Power and Data Transfer IC for Neural Prostheses with Simultaneous 115mW Power and 2.5Mb/s Forward Data Delivery," IEEE International Solid-State Circuits Conference (ISSCC), San Francisco, CA, USA, pp. 472-474, Feb. 2021.

PCT International Search Report and Written Opinion issued in International Application No. PCT/US2023/068574, mailed Nov. 6, 2023.

Piech et al., "A wireless millimetre-scale implantable neural stimulator with ultrasonically powered bidirectional communication," *Nat. Biomed. Eng.*, 4:207-222, Feb. 2020.

Singer et al., "Magnetoelectric Materials for Miniature, Wireless Neural Stimulation at Therapeutic Frequencies," Neuron, 107(4):631-643, 2020.

Tang et al., "A Wireless Power Transfer System with Up-to-20% Light-Load Efficiency Enhancement and Instant Dynamic Response by Fully Integrated Wireless Hysteretic Control for Bioimplants," IEEE International Solid-State Circuits Conference (ISSCC), San Francisco, CA, USA, pp. 470-472, Feb. 2021.

Thimot et al., "A 27-Mbps, 0.08-mm$^3$ CMOS Transceiver with Simultaneous Near-field Power Transmission and Data Telemetry for Implantable Systems," *Proc Cust Integr Circuits Conf.*, Mar. 2020.

Yeager et al., "A fully-integrated 10.5 μW miniaturized (0.125mm2) wireless neural sensor," Symposium on VLSI Circuits (VLSIC), Honolulu, HI, USA, pp. 72-73, Jun. 2012.

Yu et al., "A wireless network of 8.8-mm3 bio-implants featuring adaptive magnetoelectric power and multi-access bidirectional telemetry," 2022 IEEE Radio Frequency Integrated Circuits Symposium (RFIC), Denver, CO, USA, pp. 47-50, 2022.

Yu et al., "MagNI: A Magnetoelectrically Powered and Controlled Wireless Neurostimulating Implant," IEEE Transactions on Biomedical Circuits and Systems, 14(6):1241-1252, 2020.

Yu et al., "Multisite bio-stimulating implants magnetoelectrically powered and individually programmed by a single transmitter," IEEE Custom Integrated Circuits Conference (CICC), Austin, TX, USA, pp. 1-2, Apr. 2021.

Zhu, "Methods of frequency tuning vibration based microgenerator," Dissertation, University of Southampton, 2009.

Office Action issued in Japanese Application No. 2024-573851, mailed May 7, 2025, and machine translation thereof.

\* cited by examiner (a) Conceptual view of the proposed BioNet with adaptive power transfer and bi-directional telemetry and
(b) a photo of the 8.8mm³ implants Block diagram of the bio-implant and the wearable external TRX Existing modulation schemes for simultaneous wireless power and data transfer: (a) OOK, ASK-PWM, and ASK-PPM and (b) frequency splitting FSK; and (c) proposed notch-spacing time-domain modulation.

Schematics and operation waveforms of the frequency-locking-based local timing reference generation.

Existing multiple-access uplink telemetry strategies: (a) TDMA, (b) FDMA with different carrier frequency, and (c) FDMA with analog modulation; and (d) principles of the proposed FDMA with individually programmed IF.

(a) Schematics of the FDMA backscatter circuitry and the operating waveform; (b) schematic of the VCO for implant input voltage sensing; and (c) schematic of the programmable IF signal generator.

Block diagram of the proposed closed-loop global power control.

(a) implant chip micrograph; (b) illustration of the in-vitro test with 2-cm porcine tissue and (c) schematics of the external TRX's backscatter RX and the in-vitro test setup.

(a) Measured waveforms of the implant's normal operation with simultaneous power and downlink data transfers; and (b) zoom-in view of the measured frequency calibration of clock recovery.

Measured clock CLK$_{LO}$ locking of (a) 15 devices and (b) with 1.3-to-3.3-V input voltages variations; and (c) measured IF frequency with individual downlink programming.

(a) Measured waveforms of uplink data demodulation with 140-kHz IF frequency and 40- kbps data rate and (b) implant voltage feedback.

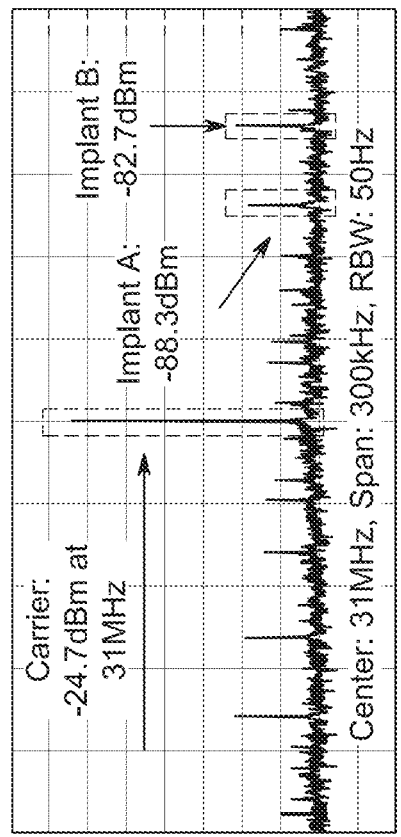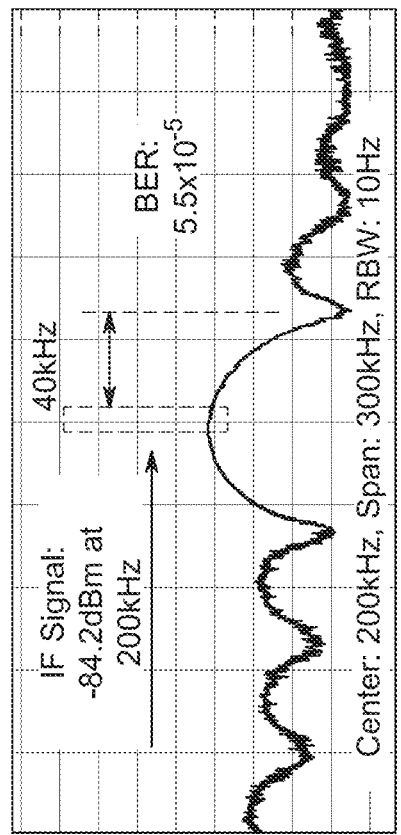
FIG. 26
Spectrums of the uplink tested with (a) 40-kbps PRBS and (b) simultaneous backscattering of two implants whose uplink IF frequencies are individually programmed, all tests are conducted in vitro.

Measured sample operations of global wireless power transfer control against device movements: external TRX-implant distance (a) increases from 2 cm to 3.5 cm and (b) decreases from 3.5 m to 2.5 cm.

Measured (a) received voltage, power transfer efficiency and (b) uplink BER at various distances between the external TRX and the implant.

|  |  | This Work | Nat. BME'20 [5] | JSSC'19 [2] | CICC'19 [3] |
|---|---|---|---|---|---|
| Technology | | 180 | 65 | 65 | 65 |
| Bio-Function | | Stimulation | Stimulation | Recording | Recording |
| Power | Link | ME | Ultrasonic | Ultrasonic | Inductive |
| | Harvester Size | $0.8mm^3$ ME Film | $0.4mm^3$ Piezo | $0.6mm^3$ Piezo | $0.25mm^2$ Coil |
| | Peak PTE at Distance (mm) | 5% at 0 0.2% at 20 | 0.06% at 18 | N/A | 0.06% at 10 |
| | Global Control? | Yes | No | No | No |
| DL Data | Link | ME | Ultrasonic | N/A | Inductive |
| | $f_{carrier}$ (MHz) | 0.34 | 1.85 | | 900 |
| | Modulation Scheme | Time Modulation | AM | | ASK-PWM |
| | Data Rate (kbps) | Max: 62.3 | N/A | | 1000 |
| | DR/$f_{carrier}$ | 0.18 | N/A | | 0.0011 |
| | Individually Addressable? | Yes | No | | Yes |
| UL Data | Link | Inductive | Ultrasonic | Ultrasonic | Inductive |
| | $f_{carrier}$ (MHz) | 31 | 1.85 | 1.78 | 900 |
| | Scheme | LSK | LSK | LSK | LSK |
| | Data Rate (kbps) | 40 | N/A | 35 | 10000 |
| | Multiple Access? | FDMA with Programmable IF | No | FDMA w Diff. $f_{INPUT}$ | TDMA |
| | BER | 1.00E-04 | N/A | N/A | N/A |
| SoC Power (μW) | | 11 | 4 | 37.7 | N/A |
| Implant Size (mm³) | | 8.8 | 1.7 | 0.8 | N/A |
| Max. Distance (mm) | | 60 | 55 | 50 | 10 |

FIG. 29

| VLSI'21 [12] | CICC'20 [11] | ISSCC'21 [13] | ISSCC'21 [9] |
|---|---|---|---|
| 180 | 180 | 180 | 180 |
| Recording | No | No | No |
| Optical | Inductive | Inductive | Inductive |
| N/A | 4mm² Coil | 706mm² Coil | 462mm² Coil |
| N/A | 1.04% at 1 | 89.6% at 5 | N/A |
| No | No | No | Yes |
| Optical | Inductive | Inductive | N/A |
| N/A | 27 | 6.5, 7.5 | |
| ASK-PWM | ASK | FSK | |
| N/A | 6.6 | 2500 | |
| N/A | 0.00024 | 0.38 | |
| Yes | No | No | |
| Optical | Inductive | | Inductive |
| N/A | 700 | | 6.78 |
| PWM | LSK | N/A | LSK |
| 0.3 | 27000 | | N/A |
| No | No | | No |
| N/A | 1.00E-04 | | N/A |
| 0.57 | N/A | N/A | N/A |
| N/A | N/A | N/A | N/A |
| N/A | 2.5 | 5 | N/A |

FIG. 29 (Continued)

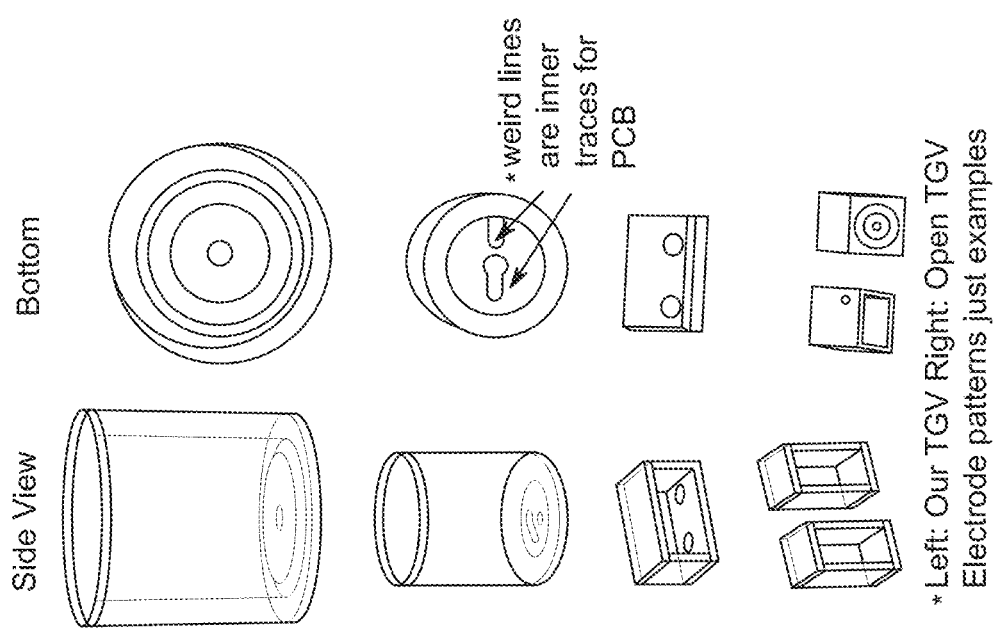

| Design | TGV Wafer | Glass Tube/Spacer | Total Volume (mm³) |
|---|---|---|---|
| 1) Current Design: Flex/Rigid PCB, manufacturable | Schott-Our design | FD Glass Cylinder OD: 9mm ID: 7mm Total Height: 9mm | 570 |
| 2) Smaller version, Same electrodes as current design, board wired directly to cap | Schott-Our design | FD Glass Cylinder OD: 6mm ID: 4mm Total Height: 7mm | 200 |
| 3) Horizontal Box, two electrodes on bottom, similar to evns design | Schott-Our design | FD Glass Rectangle Inner Size: 2x4mm Wall: 0.5mm Total Height: 3mm | 45 |
| 4) Vertical Box, two electrodes on bottom, alternative TGV cap designs | Schott-Our design or open one | FD Glass Rectangle Inner Size: 2x2mm Wall: 0.3mm Total Height: 5mm | 33 |

FIG. 35

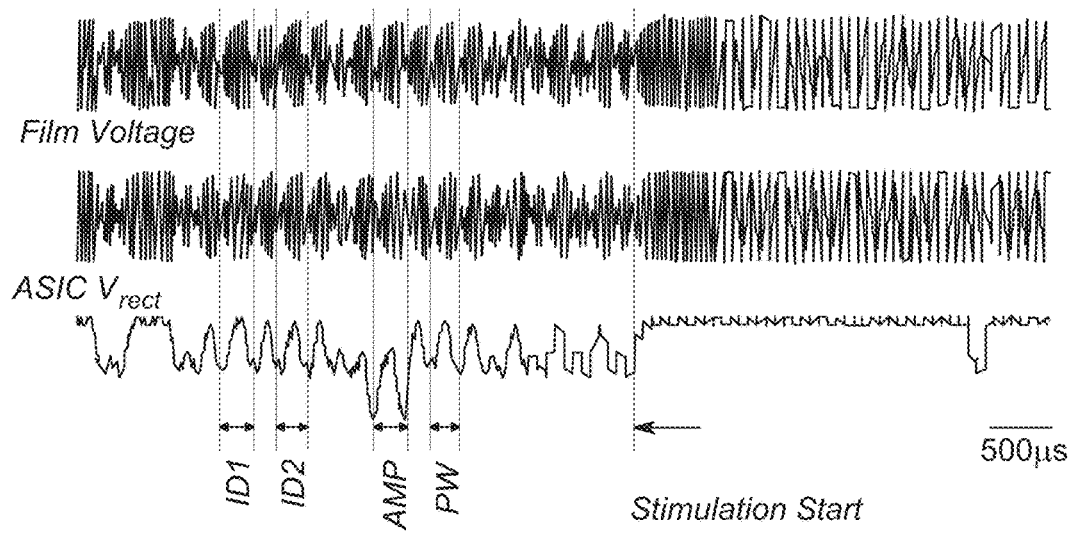
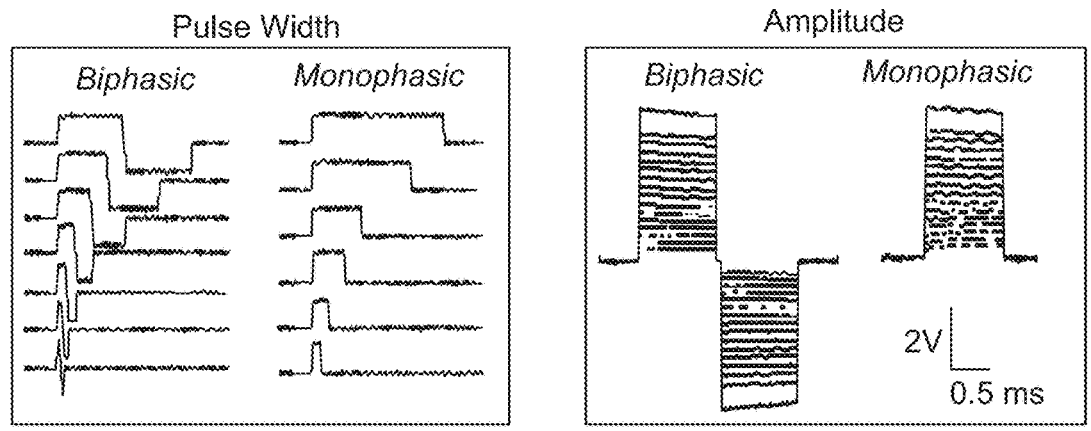
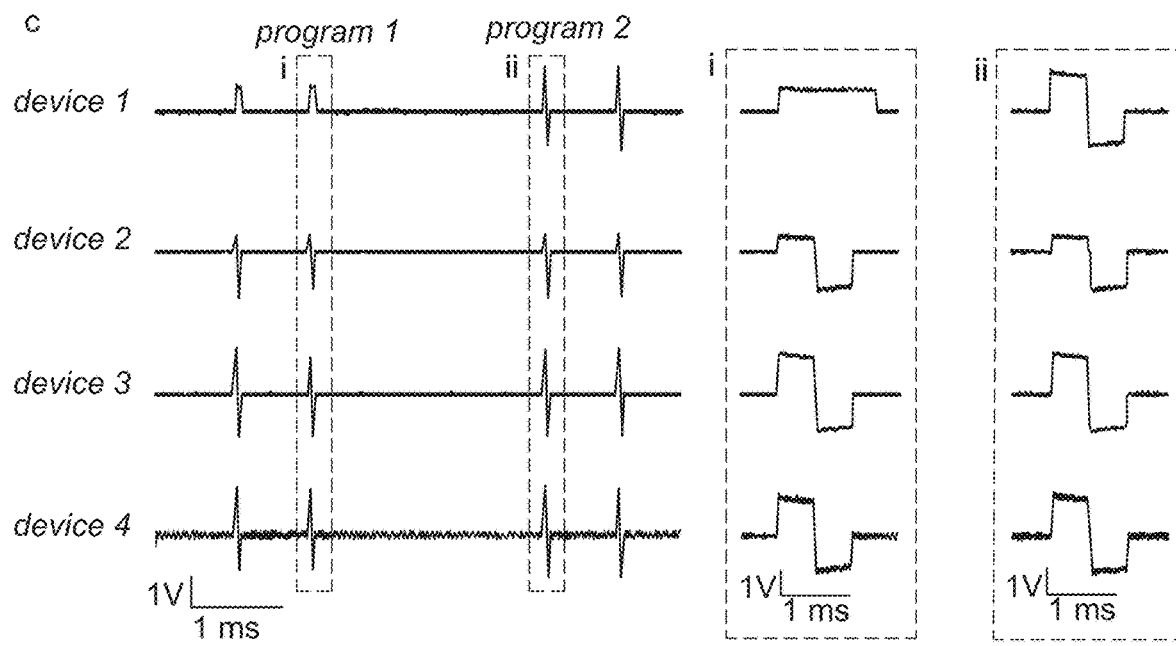
FIG. 40

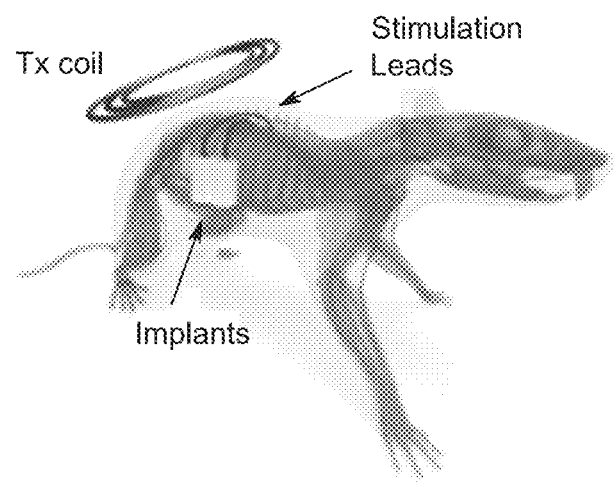
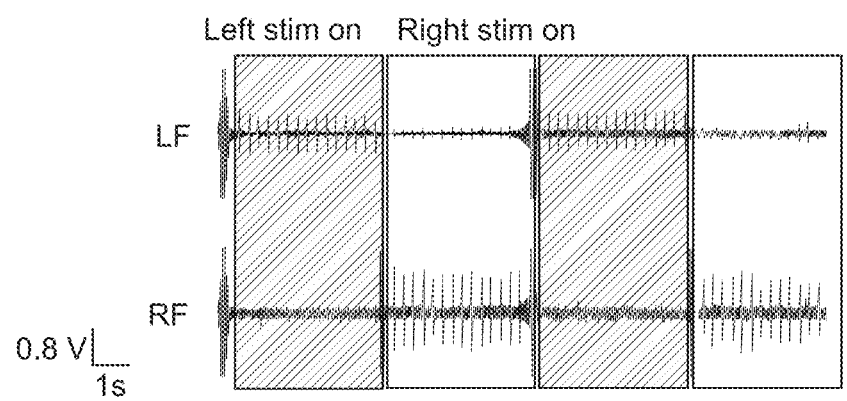
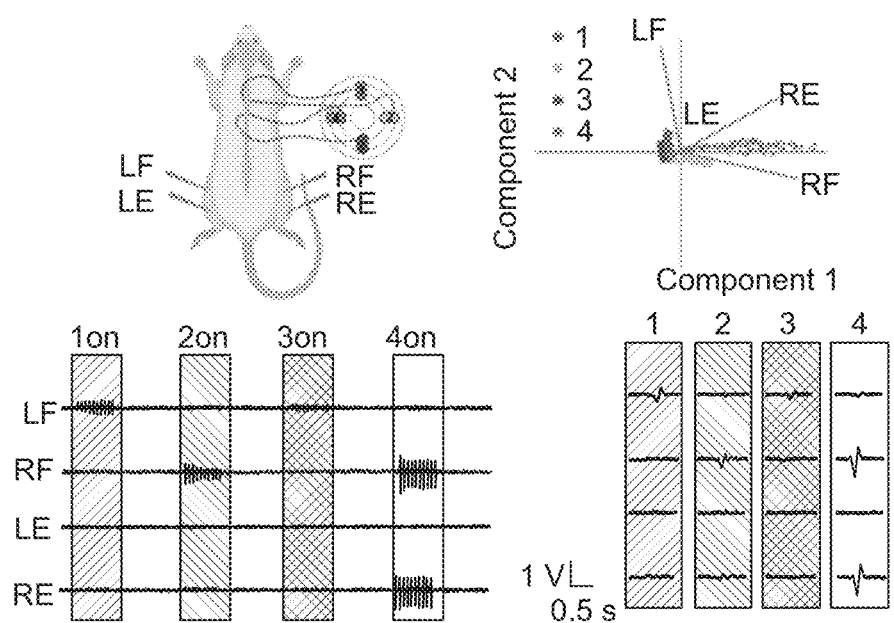
FIG. 42

SYSTEMS AND METHODS FOR WIRELESS COMMUNICATION WITH IMPLANTABLE DEVICES

CROSS-REFERENCE TO RELATED APPLICATIONS

This application is a divisional of U.S. application Ser. No. 18/336,787, filed Jun. 16, 2023, which claims priority to U.S. Provisional Application No. 63/353,371, filed Jun. 17, 2022, the entire contents of each of which are incorporated herein by reference.

STATEMENT REGARDING FEDERALLY SPONSORED RESEARCH

This invention was made with government support under Grant No. ECCS-2023849 awarded by the National Science Foundation, Grant No. U18EB029353 awarded by the National Institutes of Health and Grant No. FA8650-21-2-7119 awarded by the Defense Advanced Research Projects Agency. The government has certain rights in the invention.

BACKGROUND

A. Field

This disclosure relates to apparatus and methods providing a passive, power-efficient backscattering communication system that enables transmitting data wirelessly between implantable magnetoelectric (ME) devices and an external base station.

B. Related Art

Bioelectronic implants, which can therapeutically target specific tissue sites without large doses of traditional pharmaceuticals, are emerging as a promising option for personalized medicine. However, as these devices become smaller and less invasive, it is challenging to develop similar functionality to larger battery powered implants due to the difficulties in power and data delivery. Recent developments in miniature wirelessly powered electrical stimulators, while promising, are often limited to one or two stimulation channels, which limits the application space compared to traditional stimulators. Wireless techniques based on ultrasound and inductive coupling have made significant progress in overcoming this with a transition to single transmitter/multiple mote geometry. However these methods are limited in their spatial distribution due to geometric constraints and/or power limitations.

Traditional electrical stimulators such as pacemakers, deep brain electrodes, and spinal cord stimulators, while battery powered and bulky, have shown great effectiveness in treating various disorders. In order to decrease the size and invasiveness and increase the longevity of implantable bioelectronics, some form of wireless power delivery is desired where an external transmitter delivers power to a miniature implanted "mote/s."

In comparison to traditional implants, which typically have channel counts of 4-10 stimulation channels, many newly proposed miniature implants are limited to one or two stimulation sites, which can limit their effectiveness. An effective multi-mote or multiple channels per mote system also needs to include the data transfer complexity to individually program each channel which is a further challenge for a wireless system where each mote may not be in the same alignment with the transmitter.

Accordingly, the successful implementation of implanted powered devices poses numerous challenges. For example, a fundamental issue for bioelectronics is the ability to deliver power to miniature devices inside the body. Wires provide efficient power transmission, but are common failure points and limit device placement. Wireless power by electromagnetic or ultrasound waves must also overcome obstacles. For example, wireless power by electromagnetic or ultrasound waves must overcome absorption by the body and impedance mismatches between air, bone, and tissue. Conventional methods to wirelessly power neural implants in deep tissue regions of freely moving animals or humans are also usually bulky due to large electromagnetic coils or battery packs with external leads. In addition, the ability to provide magnetoelectric charging, data transmission and stimulation to an implantable wireless neural stimulator is not provided in existing systems.

Accordingly, a need exists to address these issues, as well as others, for the effective implementation of implanted powered devices.

SUMMARY

Briefly, the present disclosure provides systems that transmit data to an implanted devices, including neural stimulation devices, with a magnetic field.

Exemplary embodiments include a passive, power-efficient backscattering communication system that enables transmitting data wirelessly between implantable magnetoelectric (ME) devices and an external base station.

Certain embodiments encode the transmitted data through modulating the resonance frequency of a ME film by digitally tuning its electric loading conditions. Once the ME film is excited by an external pulsed magnetic field, one can record its backscattered magnetic, electric, or acoustic response by a magnetic field sensor, electrodes, or microphone, respectively. In addition, the frequency demodulation can be used to decode the data in the received signal.

Exemplary embodiments of the present disclosure include a hardware platform for wireless mm-sized bio-implant networks, exploiting adaptive magnetoelectric power transfer and novel schemes for efficient bidirectional multi-access communication. The closed-loop power control mitigates power delivery fluctuations caused by distance and alignment change and avoids redundant power of the external transceiver. The system also enables simultaneous power and time-domain modulated downlink data with a 5% peak power transfer efficiency and a 62.3-kbps maximum data rate at 340-kHz carrier frequency; multi-access uplink of all the implants enabled by individually programmed IF with a 40-kbps maximum data rate at 31-MHz carrier frequency; and more than 6-cm distance between the implant and the external TRX.

A wireless network of miniaturized battery-less bio-implants with precisely timed sensing and stimulation promises effective and flexible closed-loop and patient-specific control of physiology. By distributing multiple miniaturized implants around the targeted tissue, exemplary embodiments of the implant network disclosed herein will significantly enhance the flexibility of device deployment, better specificity and spatial resolution, and achieve less infection risks and surgery complexities [1], [2], [3], [4], than current battery-powered single-site implants.

Potential clinical applications include multisite spinal cord stimulation, nerve injury rehabilitation and cardiac pacing.

Despite decades of research, wireless power transfer (WPT) and telemetry to bio-implants remains to face critical challenges, which are even more severe for the distributed mm-sized implants. First, the WPT must be robust to ensure the proper operation of all the implants located at different positions and angles, and performing different workloads. Simply generating a strong carrier field may suffer from higher body absorption and shortened battery lifetime of the wearable power TXs [1], [2], [3], [4], [5], [6]. Non-resonant inductive coupling enables regulated WPT [7], but it requires a $k_{coupling}$ greater than 1/QRX, limiting its application in the long-distance WPT for mm-sized implants.

Closed-loop control with the help of back telemetry can regulate the received voltage effectively [8], [9]. However, existing demonstrations are all for a single cm-scale RX. Second, simultaneous power and data transfers are desired for higher power efficiency and smaller RX, but is typically restricted by tradeoffs between antenna/transducer quality factor and bandwidth [3], [10], [11], [12], [13]. Third, efficient and robust multi-access telemetries in both directions are indispensable in distributed implant networks.

Particular embodiments of the present disclosure include a system with an implanted mote and external hub, where the motes stimulate and/or record electrophysiological activity. In certain embodiments, there are one or more motes and a single transmitter, while in other embodiments, there is a single mote for each transmitter. In specific embodiments, the mote(s) are powered by magnetoelectric (ME) film, near infrared communication (NIC), and/or light (e.g. via a photodiode).

In certain embodiments, stimulation is digitally programmable based on internal circuitry in the form of an application specific integrated circuit or a microcontroller based system. In particular embodiments, the mote receives data from the external hub and data is transmitted from the hub with a modulated magnetic field, NFC, light, or bluetooth low energy. In specific embodiments, the external hub receives data from the mote and data is transmitted from the mote with ME backscatter, NFC (passive or active backscatter), light, or bluetooth low energy, and the data transmitted from the mote can contain received power. The data transmitted from the mote can contain biomarkers such as local field potential, spectragrams of the local field potential, or power in specific frequency bands such as theta band power, alpha band power, or spiking band power.

In particular embodiments, stimulation is conditioned based on data received from the mote. In certain embodiments, the system is used to apply therapy using electrical stimulation. In some embodiments, motes are implanted in or above the left and/or right dorsolateral prefrontal cortex of the brain, and in particular embodiments, motes are implanted in or above the spinal cord.

In specific embodiments, the system has stimulation sites. In some embodiments the device is a leadless stimulator, and in other embodiments b) In another embodiment, the device has leads. In particular embodiments, the stimulator has electrodes in concentric circles. In certain embodiments, the stimulator has a pair of electrodes, and in other embodiments the stimulator has a plurality of electrodes. In some embodiments, multiple devices are placed in an array or pattern to generate stimulation patterns between motes.

Certain embodiments include a wireless bioelectronic system comprising: an implantable device comprising an electrical circuit coupled to a magnetoelectric film; a magnetic field generator; and a resonant frequency modulator, where: the magnetoelectric film has a resonant frequency and the electrical circuit is configured to modulate the resonant frequency of the magnetoelectric film by applying different electric loading conditions that change a property of the magnetoelectric film.

In particular embodiments the property of the magnetoelectric film is an electric, elastic, or magnetic property of the magnetoelectric film. In some embodiments the electrical circuit is configured to modulate a voltage, resistive load, inductive load or capacitor load applied to the magnetoelectric film. In specific embodiments the magnetoelectric film comprises a piezoelectric layer, and the magnetoelectric film comprises a magnetostrictive layer coupled to the piezoelectric layer.

In certain embodiments the magnetoelectric film comprises a first magnetostrictive layer and a second magnetostrictive layer; the magnetoelectric film comprises a piezoelectric layer and the piezoelectric layer is positioned between the first magnetostrictive layer and the second magnetostrictive layer. In particular embodiments the implantable device is a first implantable device, and the wireless bioelectronic system comprises a plurality of implantable devices, wherein each implantable device comprises an electrical circuit coupled to a magnetoelectric film.

In certain embodiments the plurality of implantable devices are configured to provide neural stimulation. In particular embodiments the implantable device is coupled to a pair of electrodes. In some embodiments the implantable device is coupled to a plurality of electrodes. In specific embodiments the plurality of electrodes are arranged in concentric circles. Certain embodiments include a plurality of implantable devices placed in an array or pattern to generate stimulation patterns the plurality of implantable devices.

Particular embodiments include a wireless bioelectronic system comprising an external transceiver and a plurality of implantable devices, where: each implantable device comprises an electrical circuit coupled to a magnetoelectric film; the external transceiver is configured to simultaneously transmit a first magnetic field to each of the plurality of implantable devices; each of the plurality of implantable devices are configured to transmit a response to the external transceiver; and each of the plurality of implantable devices are configured to transmit the response to the external transceiver after the first magnetic field is transmitted from the transceiver.

In some embodiments each of the plurality of implantable devices are configured to stimulate and/or record electrophysiological activity. In specific embodiments each of the plurality of implantable devices are configured to transmit a response magnetic field to the transceiver. In certain embodiments the response magnetic field is generated by each of the plurality of implantable devices oscillating at a resonant frequency of the implantable device.

In particular embodiments the electrical circuit is configured to modulate a resonant frequency of the magnetoelectric film by applying different electric loading conditions that change a property of the magnetoelectric film. In some embodiments the transceiver comprises a magnetoelectric transmitter, a controller and a receiver. In specific embodiments the receiver is an inductive coil electrodes, or ultrasonic transducer.

In certain embodiments the plurality of implantable devices are configured to be implanted along a spinal column. In particular embodiments the response transmitted from each of the plurality of implantable devices comprises data. In some embodiments the data is transmitted from the hub with a modulated magnetic field, near field communication (NFC), light, or bluetooth low energy. In specific embodiments the data contains received power. In certain embodiments the data contains biomarkers. In particular embodiments biomarkers include local field potential, theta band power, or spiking band power. In some embodiments nerve stimulation is conditioned based on data received from the plurality of implantable devices. In specific embodiments the plurality of implantable devices are implanted in the left and/or right dorsolateral prefrontal cortex of the brain. In certain embodiments the plurality of implantable devices are implanted in or above the spinal cord.

Particular embodiments include a wireless bioelectronic system comprising an plurality of external transceivers; and a plurality of implantable devices, where: the plurality of external transceivers is uniquely paired with the plurality of implantable devices, such that each of the plurality of external transceivers selectively communicates with a single implantable device and not other implantable devices; each implantable device comprises an electrical circuit coupled to a magnetoelectric film; each external transceiver is configured to transmit a first magnetic field to an implantable device of the plurality of implantable devices; each of the implantable devices are configured to transmit a response to the external transceiver; and each of the plurality of implantable devices are configured to transmit the response to the external transceiver after the first magnetic field is transmitted from the transceiver.

Certain embodiments include a method of stimulating neural tissue, the method comprising: providing an apparatus according to the present disclosure; generating a magnetic field with one or more of the plurality of transceivers; producing an electrical output signal with the magnetoelectric film; and modifying the electrical output signal with the electrical circuit.

Particular embodiments include a method of stimulating neural tissue, where the method comprises: providing an apparatus that includes an implantable device comprising an electrical circuit coupled to a magnetoelectric film, a magnetic field generator, and a resonant frequency modulator, where the magnetoelectric film has a resonant frequency, and where the electrical circuit is configured to modulate the resonant frequency of the magnetoelectric film by applying different electric loading conditions that change a property of the magnetoelectric film; generating a magnetic field with the magnetic field generator; producing an electrical output signal with the magnetoelectric film; and modifying the electrical output signal with the electrical circuit.

Certain embodiments include a method of stimulating neural tissue, where the method comprises: providing an apparatus that includes an external transceiver and a plurality of implantable devices where each implantable device comprises an electrical circuit coupled to a magnetoelectric film, the external transceiver is configured to simultaneously transmit a first magnetic field to each of the plurality of implantable devices, each of the plurality of implantable devices are configured to transmit a response to the external transceiver, and each of the plurality of implantable devices are configured to transmit the response to the external transceiver after the first magnetic field is transmitted from the transceiver; generating a magnetic field with the transceiver; producing an electrical output signal with the magnetoelectric film; and modifying the electrical output signal with the electrical circuit.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 26 illustrates spectrums of an uplink data of an embodiment according to the present disclosure.

FIG. 29 illustrates a table showing a comparison with state-of-the-art integrated power and telemetry platforms for wireless bio-implants.

FIG. 35 illustrates options for glass packaging design and electrode spacing in embodiments according to the present disclosure.

FIG. 40 illustrates operational aspects of a network of four individually addressable implants according to an embodiment of the present disclosure.

FIG. 42 illustrates an embodiment of the present disclosure implemented for stimulation of a rat spinal cord.

DETAILED DESCRIPTION OF THE INVENTION

Embodiments of the present disclosure include a passive, power-efficient backscattering communication system that enables transmitting data wirelessly between implantable magnetoelectric (ME) devices and an external base station.

Embodiments of the present disclosure also include a wireless bioelectronic system comprising a magnetic field generator and an implantable device comprising an electrical circuit coupled to a magnetoelectric film. Particular embodiments include a backscatter communication system leveraging the magnetoelectric material tunability features to enable bidirectional wireless communication link for magnetoelectric Bio-implant (ME-BIT). The ME-BIT combines (1) ME film fabricated using a piezoelectric layer and a magnetostrictive layer that are mechanically coupled using epoxy, (2) application-specific integrated circuit (ASIC) designed using 180 nm complementary metal-oxide-semiconductor (CMOS) technology.

Figure 1:
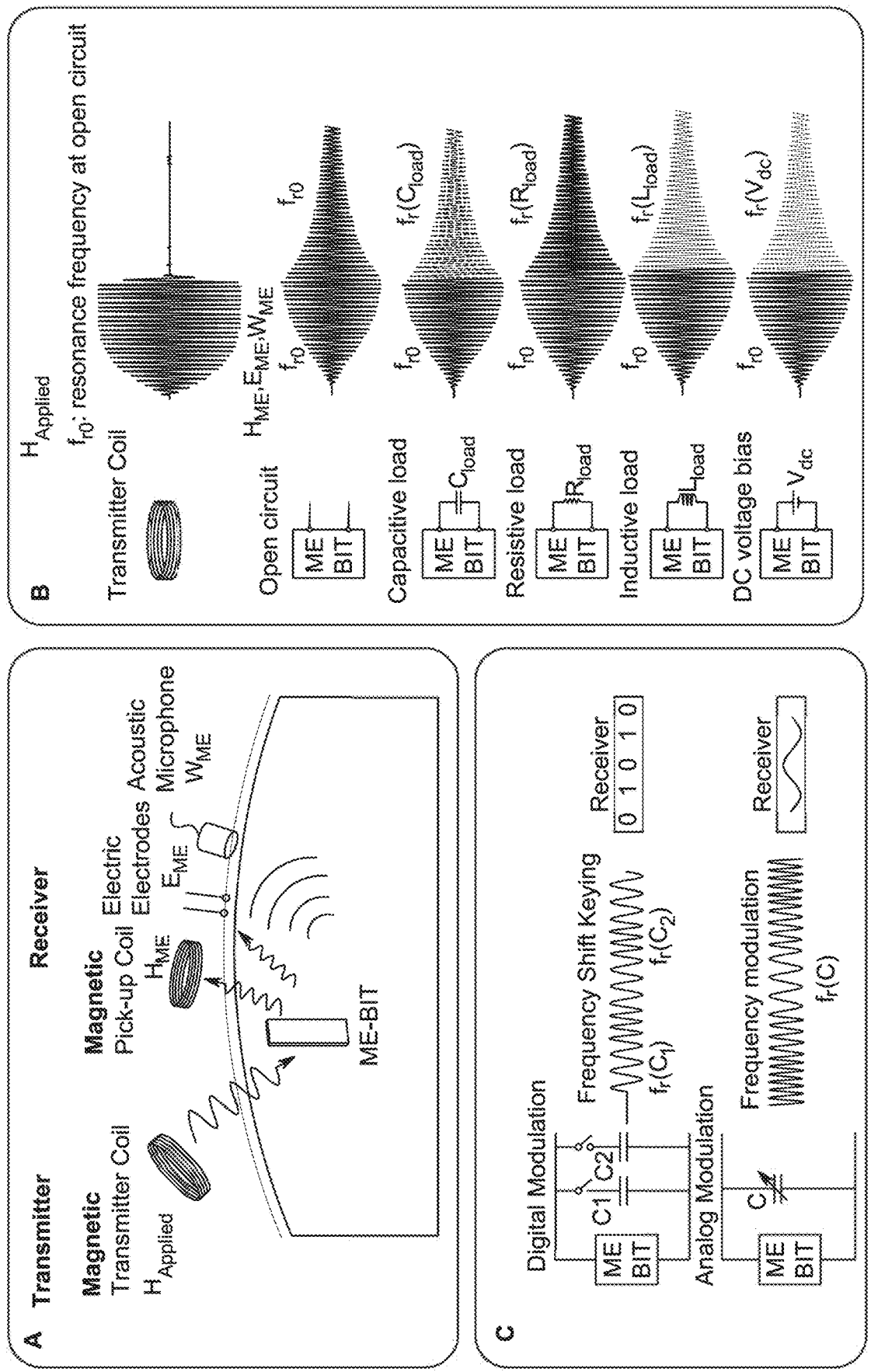
FIG. 1 illustrates a schematic of an embodiment according to the present disclosure.

As shown in FIG. 1.A, when we excite the ME-BIT by an external pulsed magnetic field, mechanical vibrations are generated in the magnetostrictive layer due to the direct magnetostriction effect. Due to the converse magnetostriction effect, the film generates a backscattered magnetic field that we can detect using a pick-up coil. The mechanical vibrations form acoustic waves that travel through tissues, and we can detect them using a microphone at the skin surface. Due to the mechanical coupling between the magnetostrictive layer and the piezoelectric layer, the mechanical vibrations transferred to the piezoelectric layer generate an electric field across the film. We can detect the generated electric field using a pair of electrodes at the skin surface due to the conductive properties of the tissue.

To eliminate the interference between the stimuli field and the recorded response, we take the measurements during the ringdown period where the external field is off, and we determine the resonance frequency by computing the Fast Fourier Transform (FFT) of the ringdown waveform. To encode the transmitted data from the implant to an external base station, we electrically modulate the resonance frequency of the ME film by connecting its terminals to different electric loading conditions that change its electric, elastic, or magnetic properties hence changing its resonance frequency. As shown in FIG. 1.B, the DC voltage, resistive load, inductive load, or capacitor load can shift the resonance frequency of the ME film, hence enabling frequency modulation.

Both analog modulation and digital modulation are possible as shown in FIG. 1.C. For example, to transmit an analog signal, we use different capacitors to continuously change the resonance frequency. For a digital signal, we use a frequency-shift keying scheme where two capacitive load values are used to represent the digital 0 and digital 1 data. In addition to the frequency, these loading conditions change the response amplitude, hence amplitude modulation techniques can be used to encode the data. In both cases, the ASIC will tune the dc voltage, resistive, inductive, or capacitive loads through various analog and/or digital modulation schemes.

In one exemplary embodiment, the ME film is fabricated using a sheet of a 30 km-thick layer of Metglas (magnetostrictive) attached using epoxy to a 270 km-thick layer of PZT-5 (piezoelectric) and then cut using a laser cutter to miniaturized 5*1.75 mm2 films. For implantation, the film is encapsulated using a protective material like parylene and the device is then delivered surgically to the target site where it is deployed. The transmitter system is built using a set of rechargeable batteries attached to custom electronics and a resonance coil that can be tuned to match the resonance frequency of the film. For the recording system, a pick-up coil, pair of electrodes, or a microphone connected to an electronic circuit is used to demodulate the received signal.

Other variants include integrating an ASIC chip for data downlink to provide a bidirectional communication link. In addition to supporting wireless power delivery and communication using the same implant. Also, amplitude or phase modulation can be used instead of frequency modulation.

Figure 2:
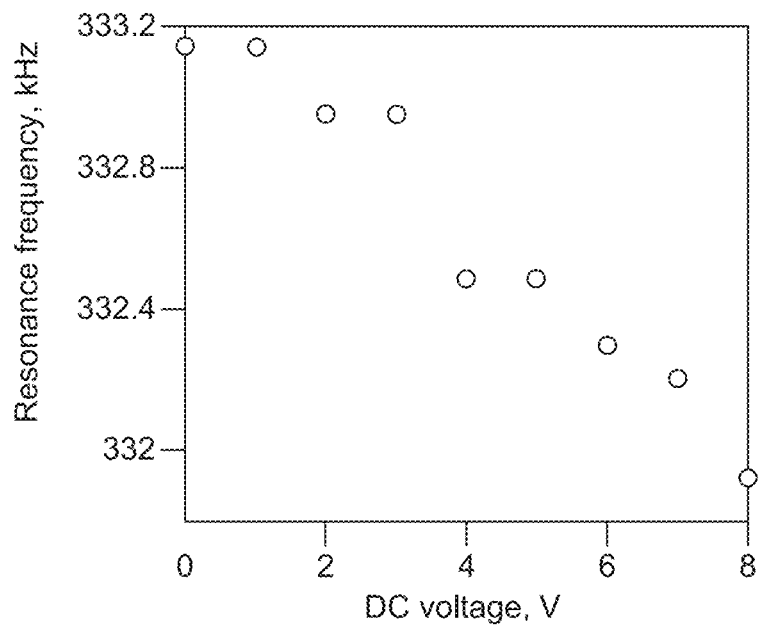
FIGS. 2-5 illustrate data from embodiments of the present disclosure.
Figure 3:
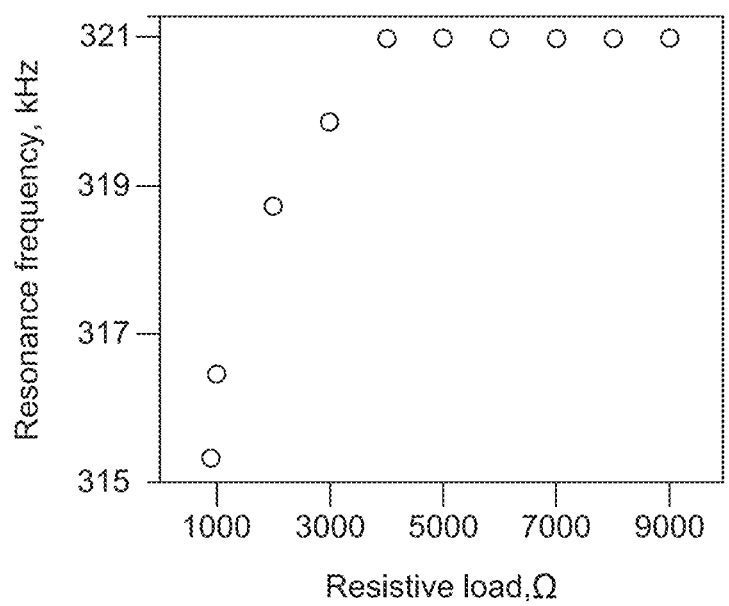
Figure 4:
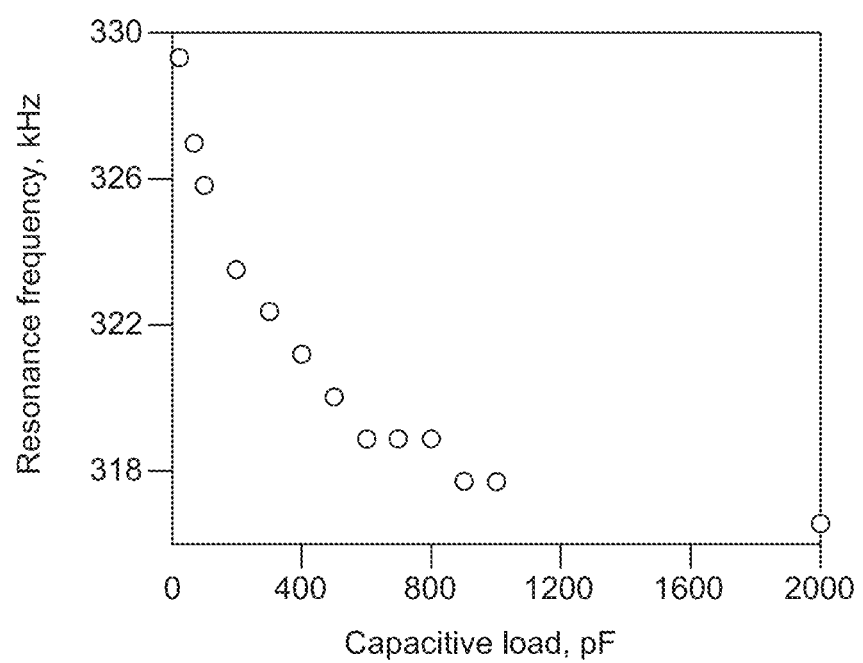
Figure 5:
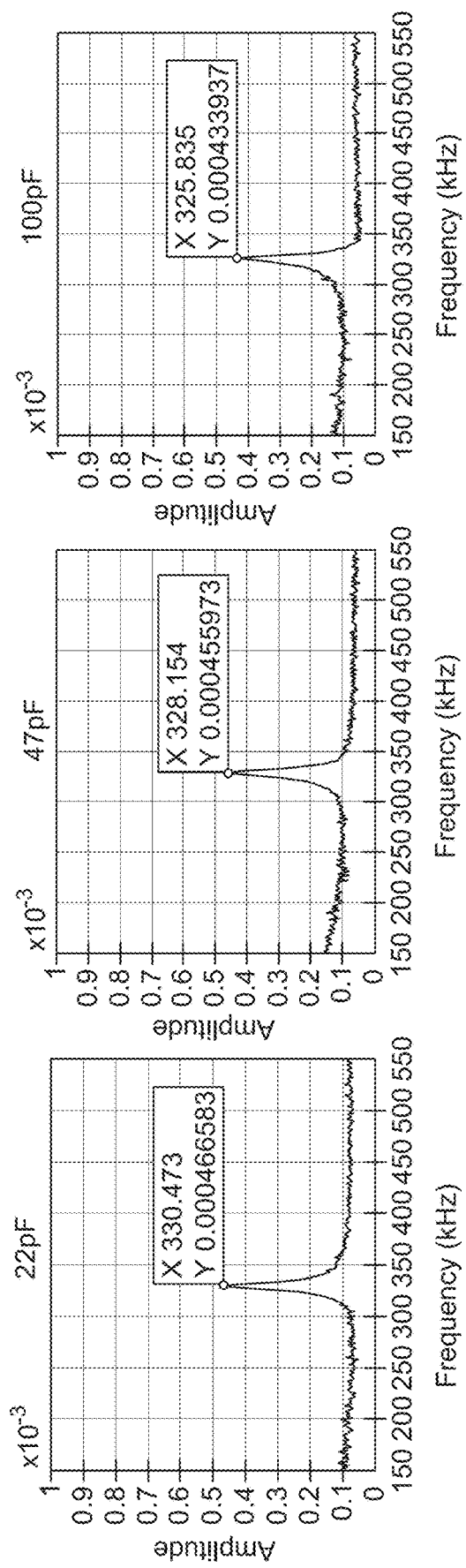
Figure 6:
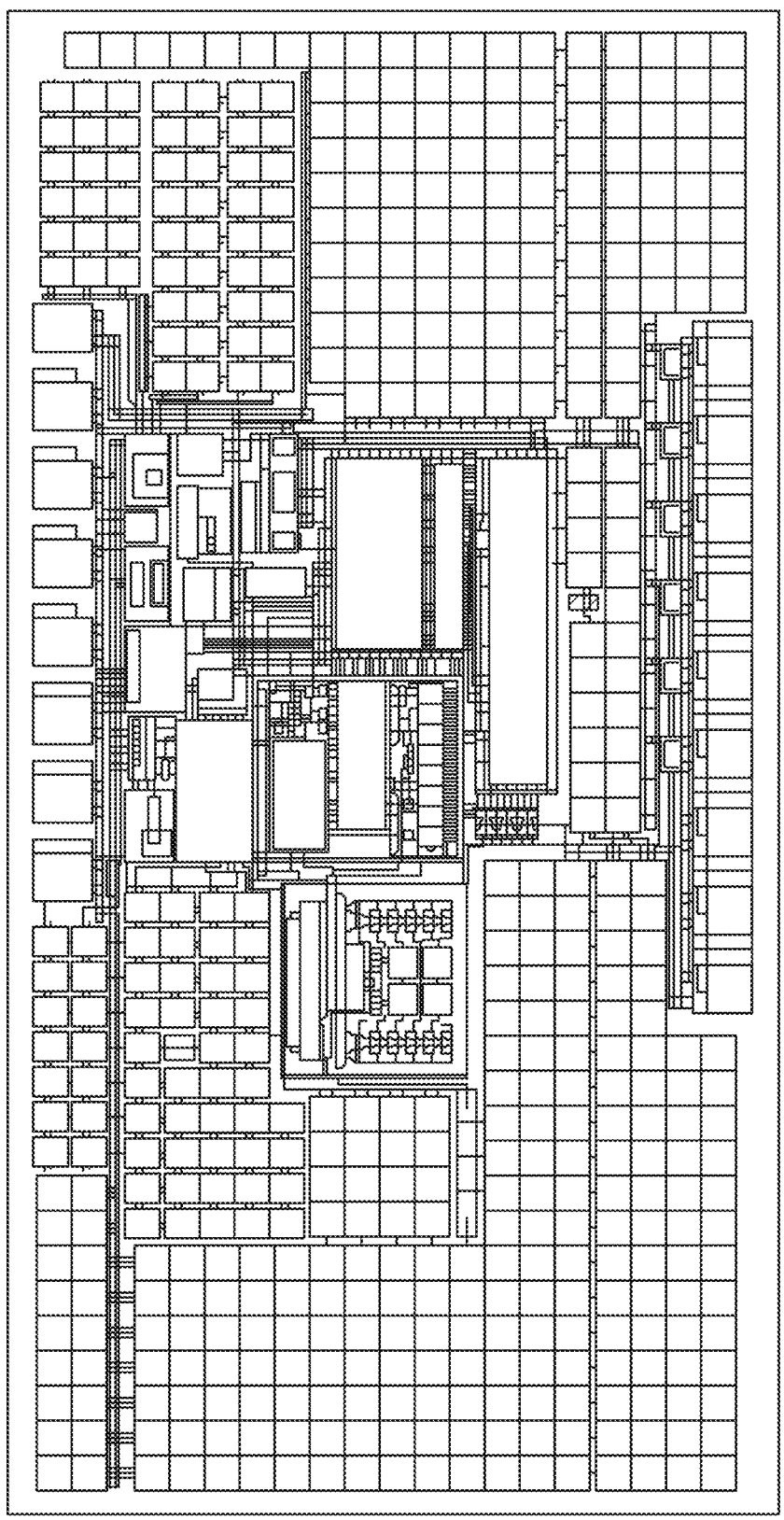
FIG. 6 illustrates a schematic of a chip design of an embodiment according to the present disclosure.

FIGS. 2-4 illustrate recorded data from exemplary embodiments, including resonance frequency of ME-BIT as a function of applied DC voltage, resistive load, and capacitive load. FIG. 5 illustrates FFT of the pick-up coil voltage during the ME film ringdown for different capacitive loads, while FIG. 6 illustrates a layout of a proof-of-principle ASIC chip design for digital frequency-shift keying (FSK) modulation of the capacitive load to realize backscattering communication. The ASIC supports ME-based power transfer and bidirectional communication.

Exemplary embodiments can be used in many different applications, including for example, closed-loop bioelectronic and distributed implants networks. Embodiments disclosed herein provide safe, reliable, and power-efficient communication systems for miniaturized implants. The strength of the backscattered signal depends on the size of the ME film, which could limit the distance of operation for smaller devices. To address this issue, the design of the receiver circuitry (coil, microphone, or electrodes) in particular embodiments can be optimized for higher sensitivity.

Figure 7:
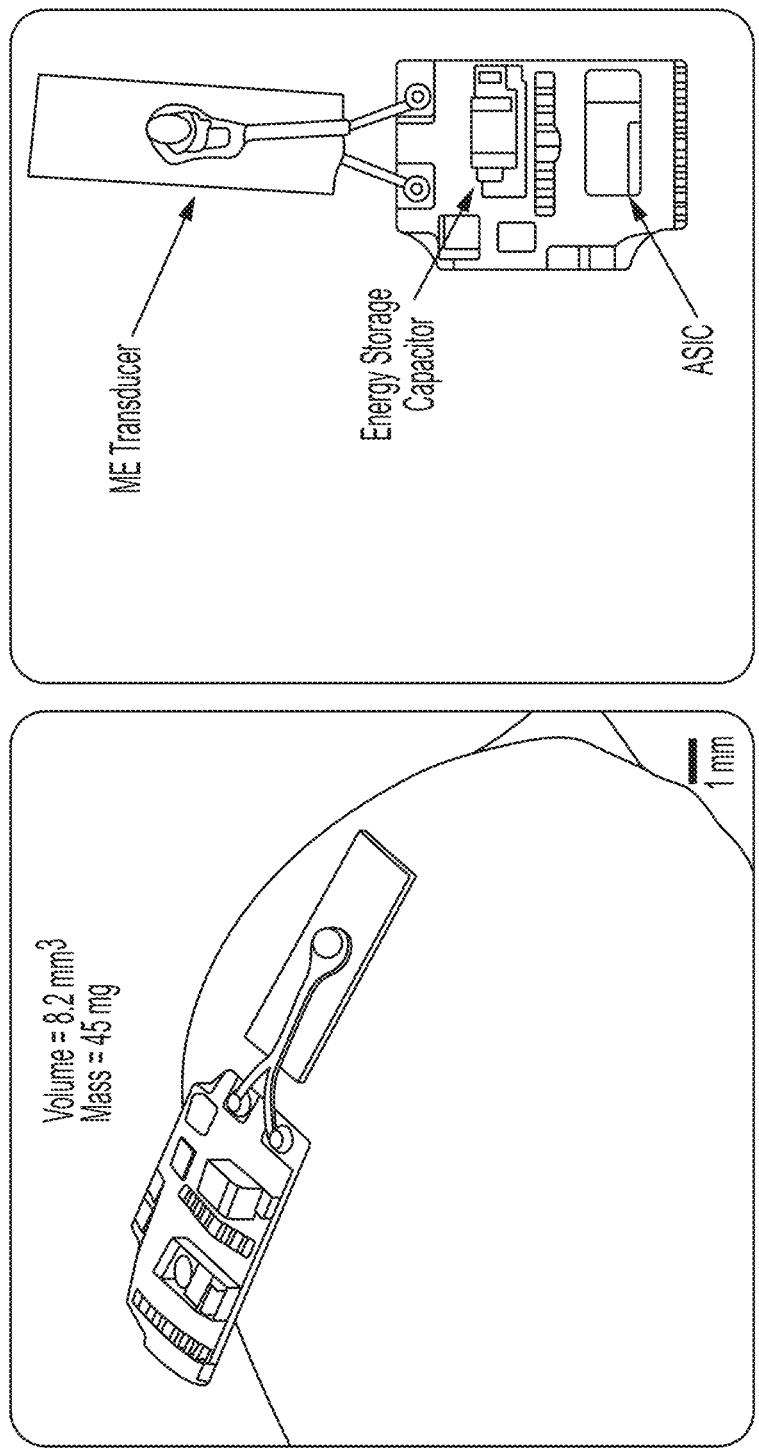
FIG. 7 illustrates a photograph of an embodiment according to the present disclosure.

FIG. 7 illustrates a prototype of a magnetoelectric implant. The implant is shown on a fingertip to demonstrate its miniaturized form factor. The implant integrates an ASIC chip, a ME transducer, and an energy storage capacitor onto the board with an 8.2-mm3 volume and a 45-mg weight.

In certain embodiments, the magnetic receiver is used to pick up the backscattered magnetic field generated by the ME film. Also, the capacitive load is used to shift the resonance frequency between two different values to digitally encode the data using frequency-shift keying.

Figure 8:
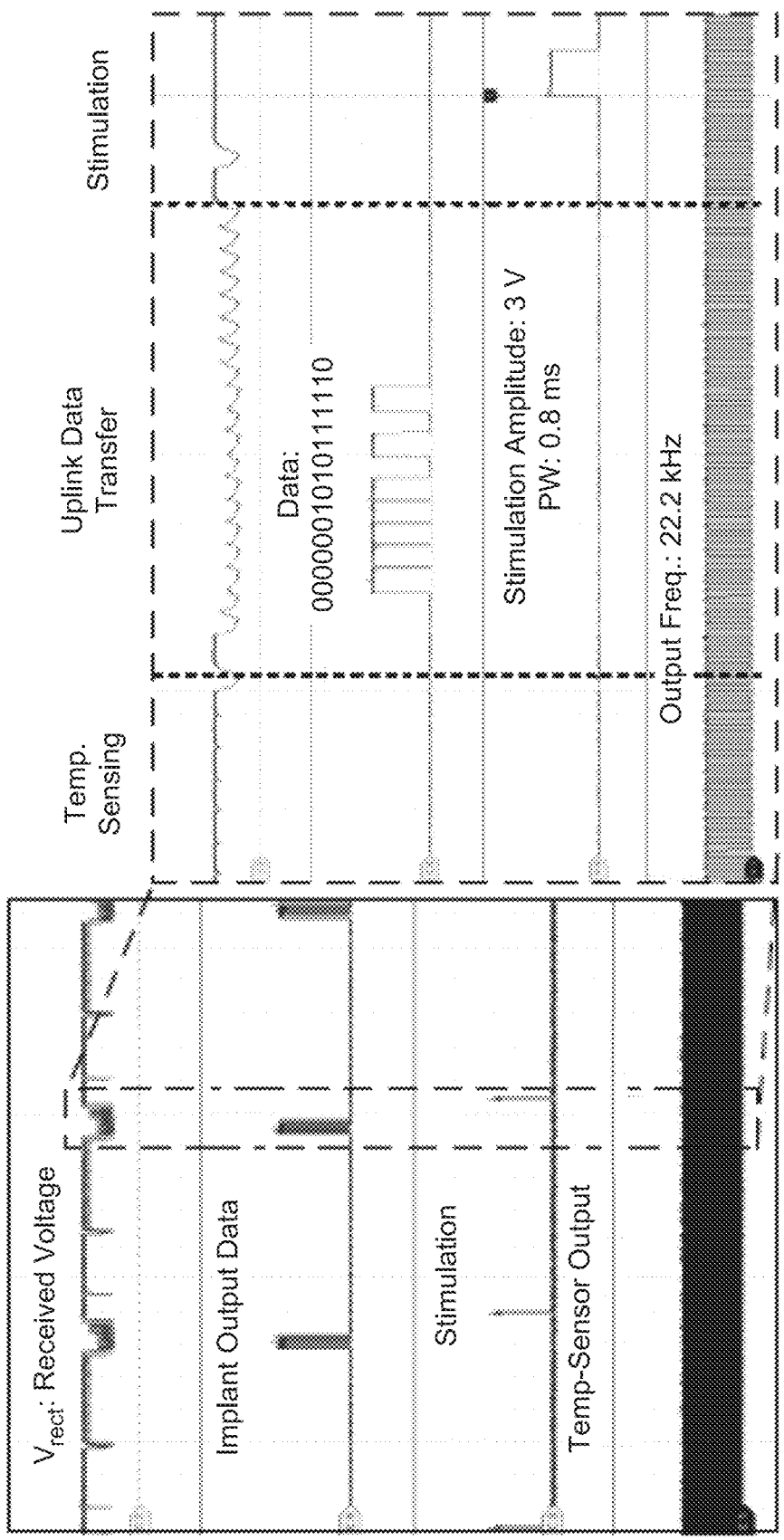
FIGS. 8-12 illustrate various representations of data associated with embodiments of the present disclosure.

FIG. 8 shows an example of the functions of the ME-BIT. The implant can harvest power for stimulation, and communicate sensor data (temperature sensor as an example) using the proposed backscatter ME technology. In particular, FIG. 8 shows the measured operation waveform of the implant. The magnetoelectrically powered and programmed implant continuously conducted temperature sensing, uplink data transfer, and stimulation; and a zoom-in view shows the implant's temperature sensor output, uplink data output, and stimulation pulse.

Figure 9:
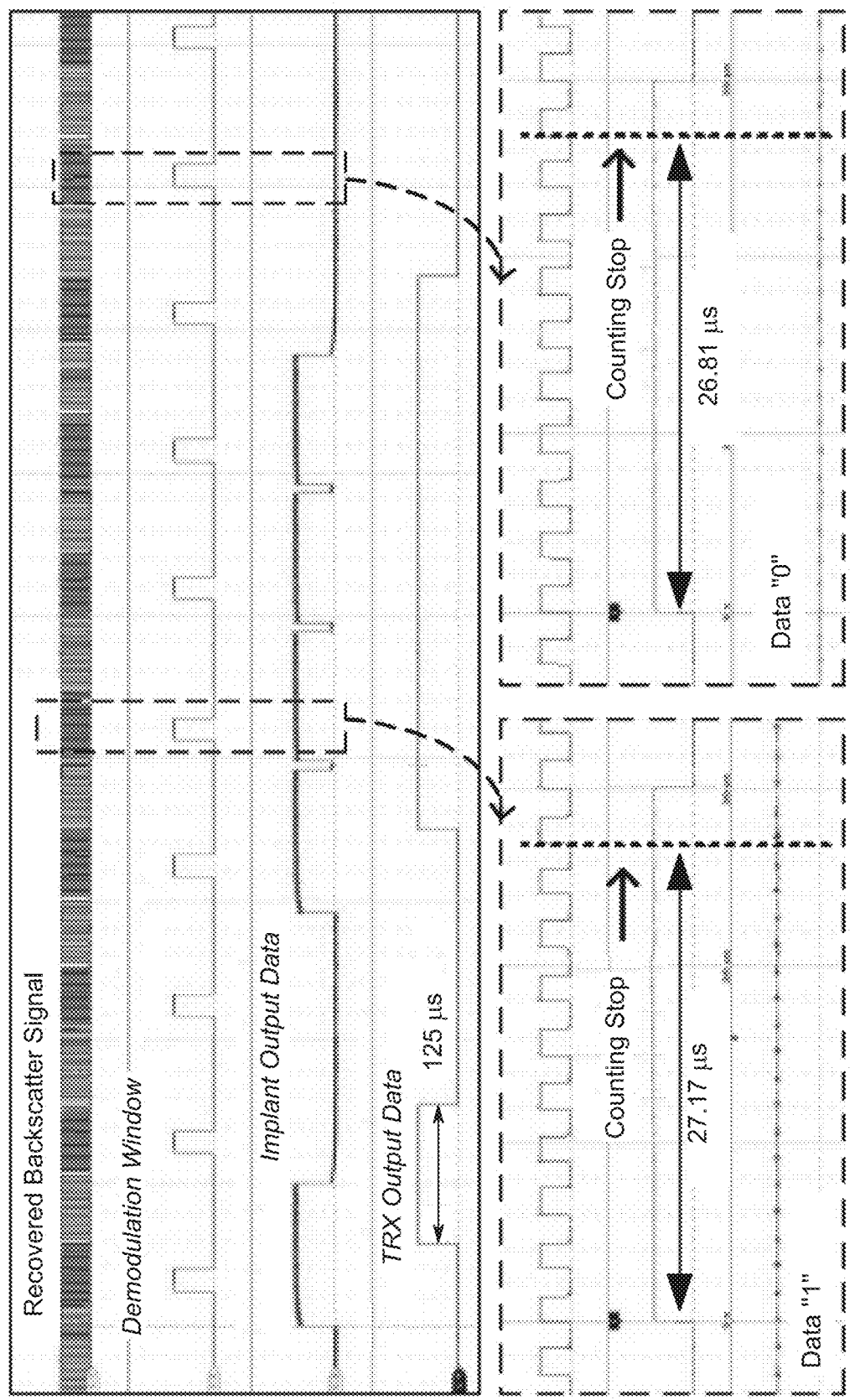

FIG. 9 illustrates measured waveforms of the demodulated signal. In particular FIG. 9 shows an example of demodulating the transmitted signal by a magnetic external transceiver. The uplink data from the implant is transmitted through ME backscatter and recovered by the external TRX. The capacitive load shift at the implant terminals, changes the frequency of the backscatter signal, resulting in different pulse widths of data "1" and "0", as shown in the zoom-in views. The data is demodulated through the detection of the pulse width change.

Figure 10:
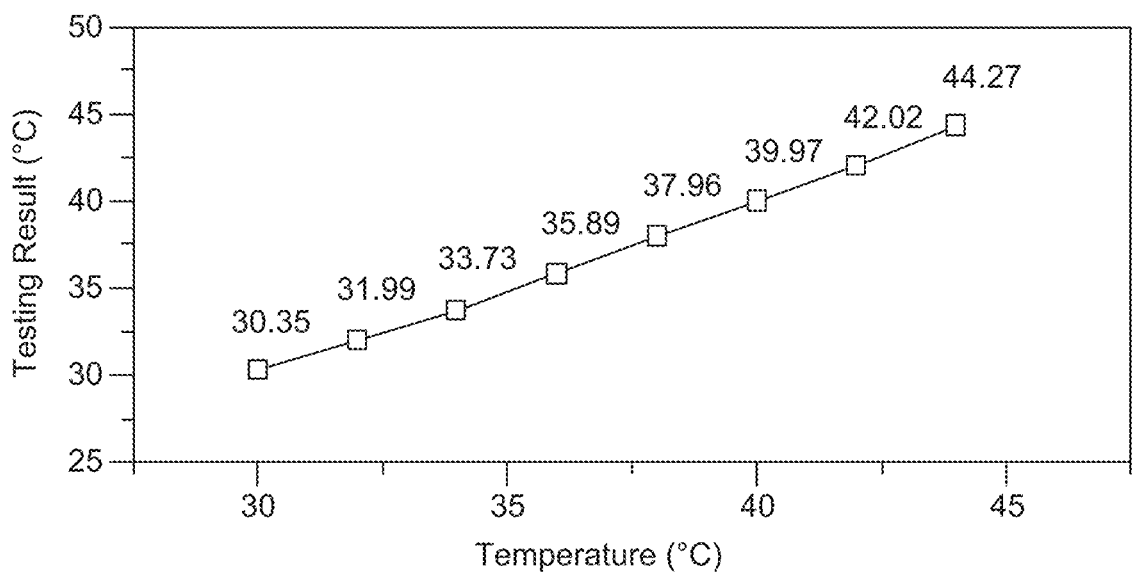

FIG. 10 shows a measured temperature sensor error of an implant. Specifically, FIG. 10 shows an example of sensor data (temperature sensor) that can be transmitted back to the receiver. The sensing results are wirelessly transmitted from the implant through ME backscatter. The implant was tested in a temperature chamber from 30° C. to 44° C., demonstrating an error smaller than 0.35° C.

Figure 11:
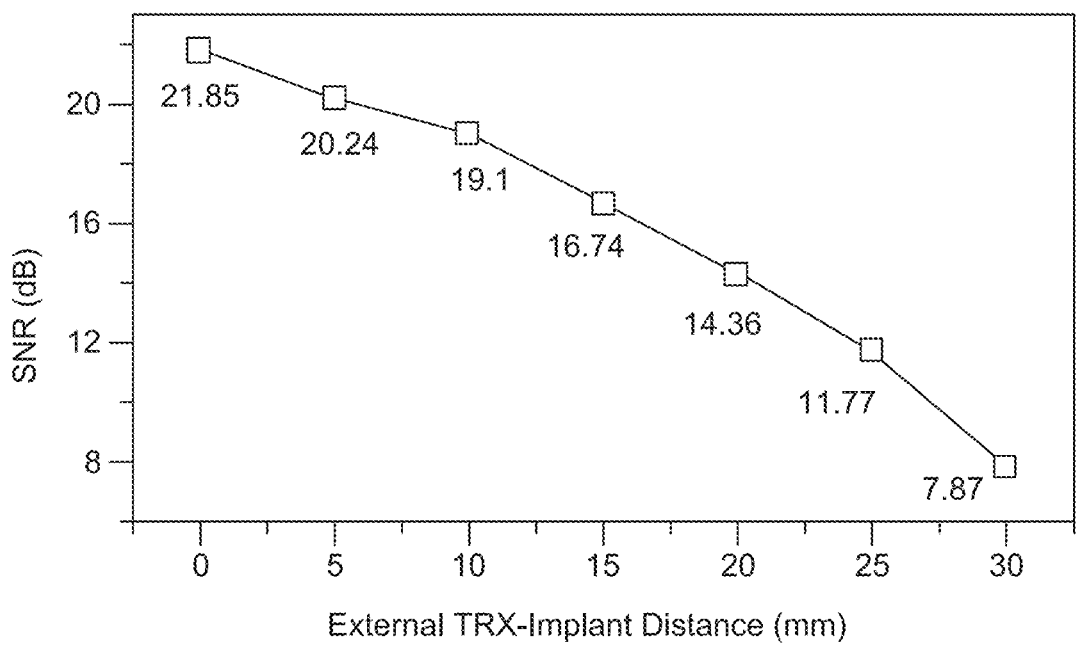
Figure 12:
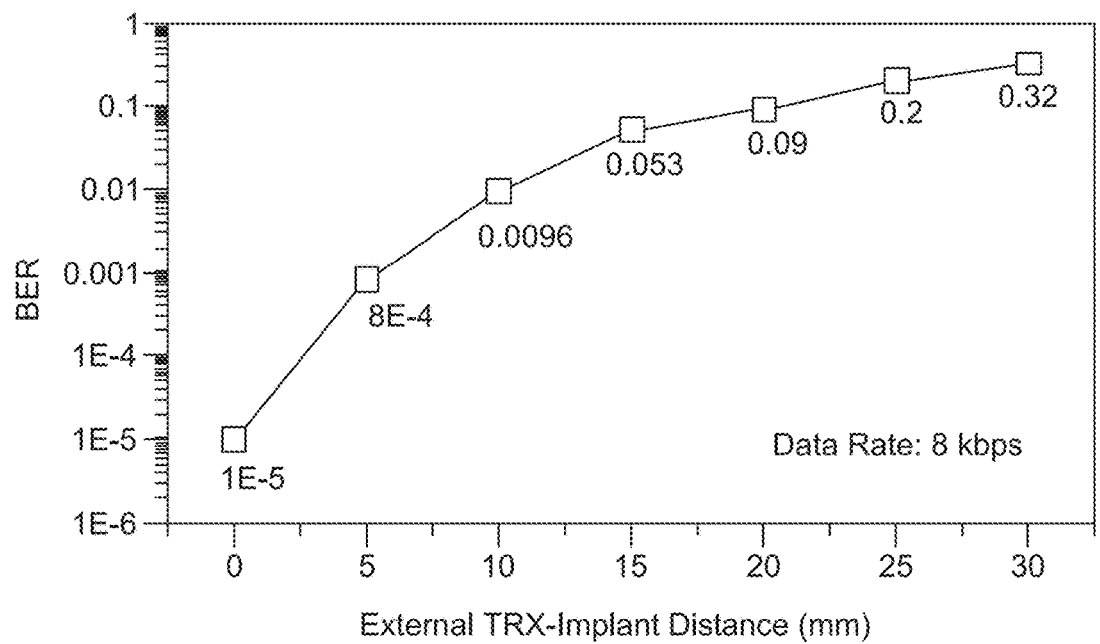

FIG. 11 illustrates an example of the communication system performance in terms of measured signal-to-noise ratio (SNR) and bit error rate (BER) at different distances from the implant. FIG. 12 shows the measured BER at various external transceiver (TRX) implant distances with a data rate of 8 Kbps.

Figure 13:
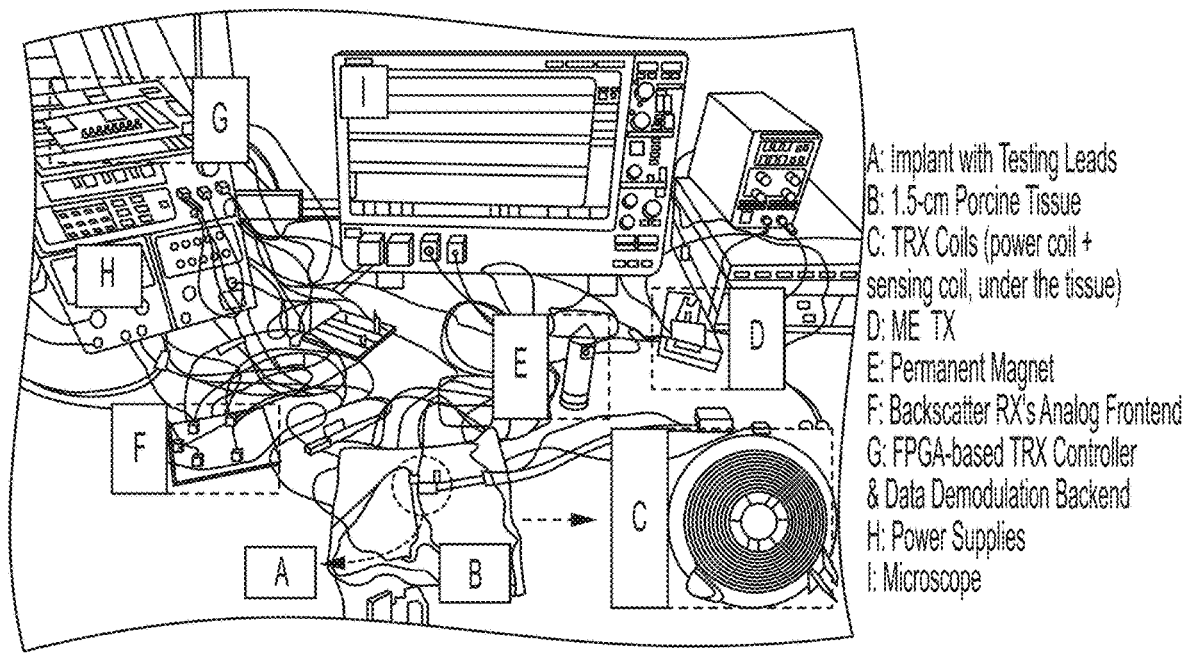
FIG. 13 illustrates an ex-vivo test demonstration of an embodiment according to the present disclosure.
Figure 14:
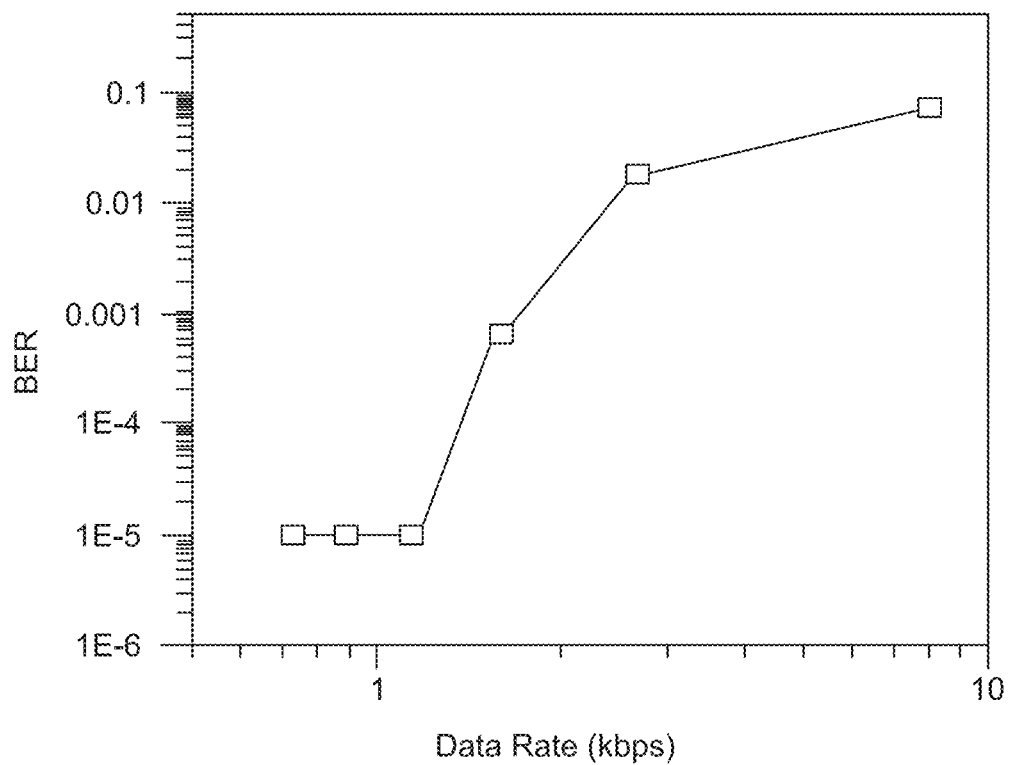
FIG. 14 illustrates data from an embodiment of the present disclosure.

FIG. 13 illustrates an ex-vivo test demonstration of the system performance using 1.5 cm thick porcine tissue. The tissue covers TRX's coils and the implant was placed on the surface of the tissue with testing leads for functionality monitoring. FIG. 14 shows an ex-vivo tested BER versus data rate.

Figure 15:
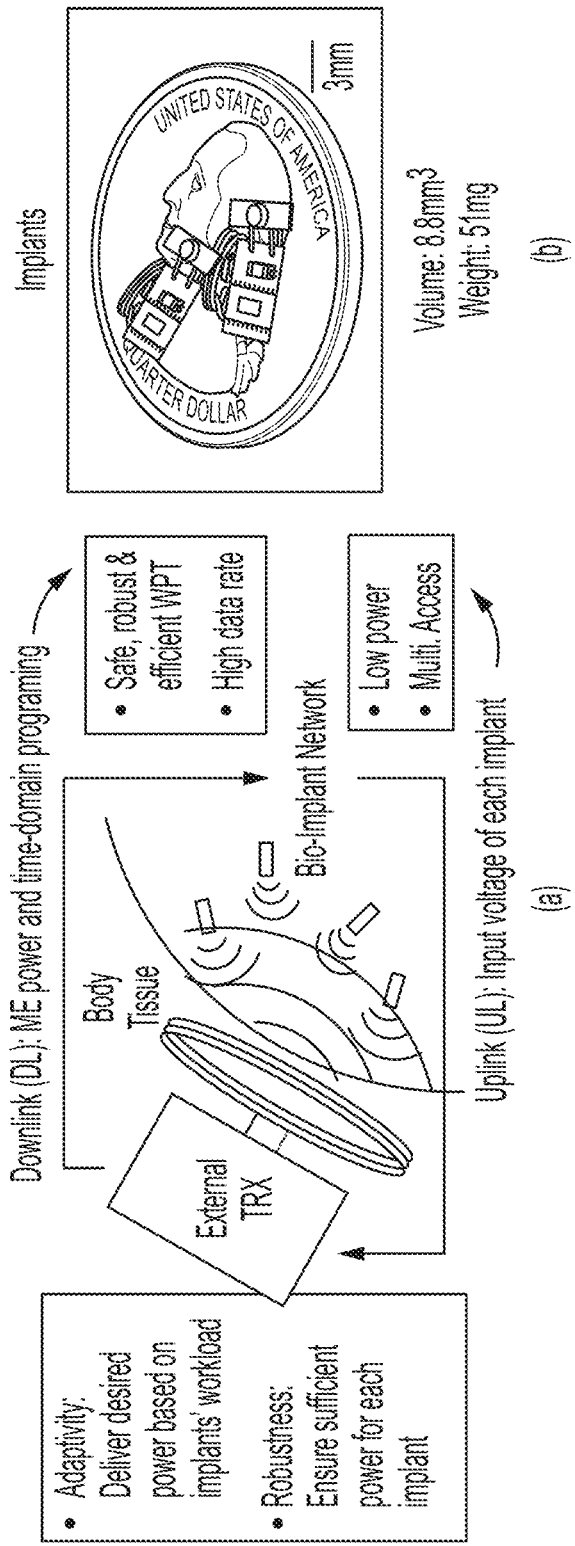
FIG. 15 illustrates a schematic and photograph of an embodiment according to the present disclosure.

To address issues of existing systems, a wireless network of mm-sized implants with closed-loop adaptive magnetoelectric power transfer regulation and is disclosed herein (sometimes referred to herein as "BioNet"). Referring now to FIG. 15 panel (a), a conceptual view of the proposed BioNet with adaptive power transfer and bi-directional telemetry is shown. FIG. 15 panel (b) illustrates a specific embodiment of the implantable device with a volume of 8.8 mm$^3$ and a weight of 51 grams.

The embodiment shown in FIG. 15(a) comprises a network that includes schemes for efficient and robust multi-access bidirectional communication The 8.8-mm3 implants shown in FIG. 15 (b) includes: (1) closed-loop magnetoelectric wireless power transfer that adapt to implants' workload, and changes of their distances and misalignments to the external TRX; (2) simultaneous power and time-domain downlink telemetry with a 5% peak power transfer efficiency (PTE) and a 62.3-kbps maximum data rate; (3) multi-access uplink telemetry enabled by individually programmed intermediate frequency (IF); (4) robust operation under 2-V source variations; and (5) a >6-cm TRX-implant working distance to receive >1.3-V power input and support 62.3-kbps downlink and 40-kbps uplink data rates.

Figure 16:
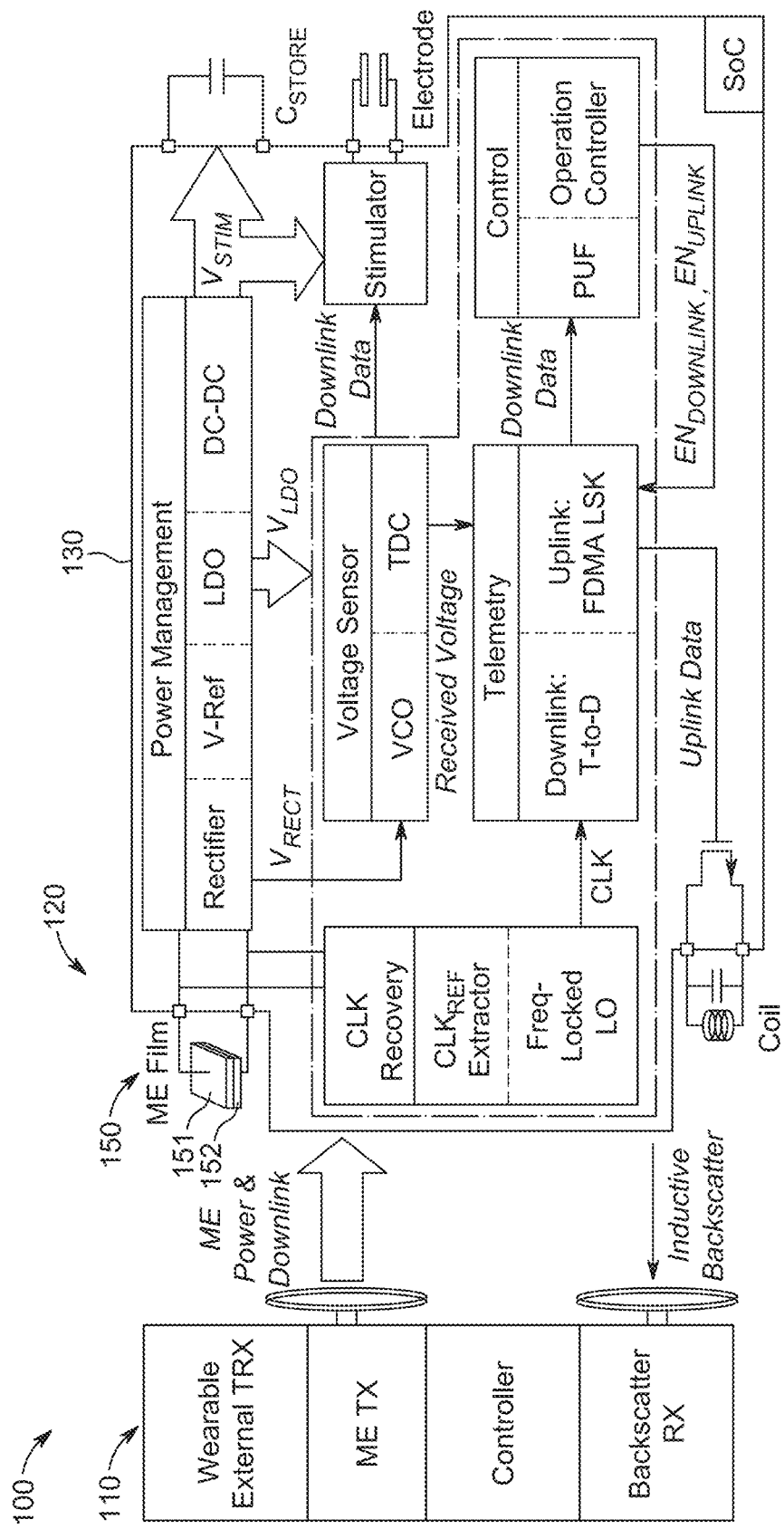
FIG. 16 illustrates a block diagram of an embodiment of the present disclosure.

FIG. 16 illustrates a block diagram of one embodiment of a system 100 comprising a wearable external transceiver 110 and an implantable device 120. In the embodiment shown, wearable external transceiver 110 comprises a magnetic field generator 111, a controller 112 and a backscatter receiver 113. In this embodiment, implantable device 120 comprises an electrical circuit 130 coupled to a magnetoelectric film 150, which further comprises a magnetostrictive layer 151 coupled to the piezoelectric layer 152. In certain embodiments, magnetoelectric film 150 may comprise additional layers or different configurations. For example, magnetoelectric film 150 may comprise a piezoelectric layer positioned between two magnetostrictive layers. In other embodiments, magnetoelectric film 150 may comprise a composite of piezoelectric and magnetostrictive elements mixed together throughout the film.

In the specific embodiment shown, electrical circuit 130 comprises a 1-mm$^2$ SoC, a 4×2-mm$^2$ ME transducer, a 2.5-mm$^2$ backscattering coil with conjugate impedance matching, and an 0.25-mm$^3$, 22-μF capacitor storing a maximum energy of 135-μJ. During operation of system 100, The implantable device 120 can recover multiple supply voltages from ME and perform bidirectional telemetry, clock recovery, input voltage sensing, and stimulation with control of external transceiver 110. System 100 is capable of magnetoelectric wireless power transfer (WPT) to an alternating current (AC) voltage. Such capabilities offer misalignment tolerance, lower tissue absorption and safe mW-level power delivery with higher PTE than inductive coupling and ultrasonic approaches [4], [10].

Downlink Data with Time-Domain Modulation

Figure 17:
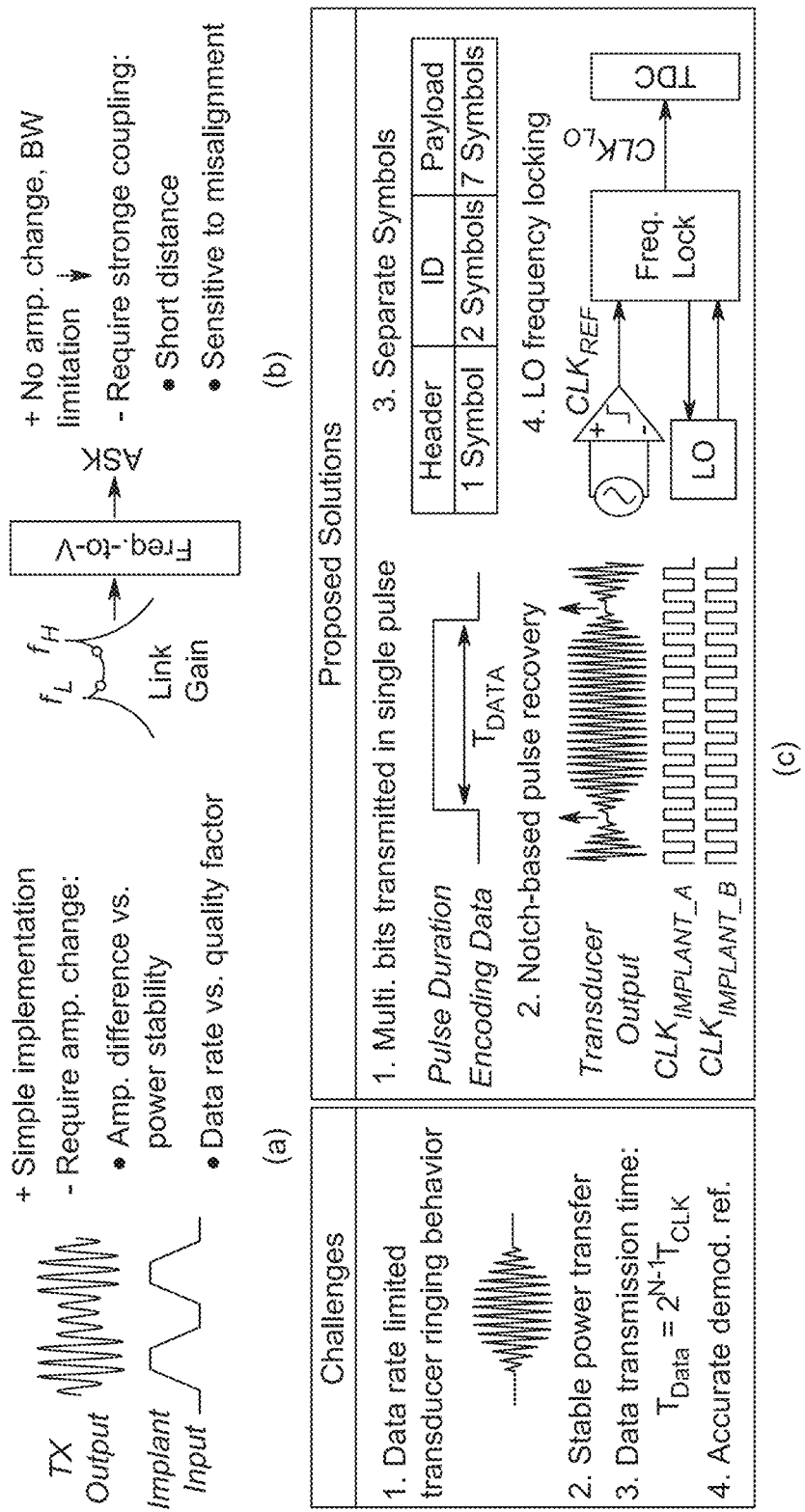
FIG. 17 illustrates a schematic of an embodiment according to the present disclosure.

Simultaneous power transfer and telemetry are highly desirable for implants with little energy storage. OOK [11], ASK-PPM [6], and ASK-PWM [3], [12] require frequent amplitude switching, leading to input power fluctuations and low data rates constrained by the high quality factor of antenna/transducer (FIG. 17 panel (a)). Frequency splitting FSK is recently proposed for stable power delivery and high data rate [13]. However, it requires strong coupling that is sensitive to distance changes and misalignment (FIG. 17 panel (b)). Exemplary embodiments of the present disclosure provide a notch-spacing time-domain modulation scheme, where multiple bits are encoded into the duration of a pulse for amortizing the transducer's low switching speed as shown in FIG. 17 panel (c). In this scheme each pulse is defined by two narrow magnetic field notches, which can be quickly detected by the active rectifier's comparators [4]. This method minimizes PTE reduction. Considering the tradeoff between switching time amortization and duration encoding overheads, each data symbol is designed to contain at most 6 bits. A complete packet includes a header, an ID for individual addressing, and a payload. An accurate clock is critical for correct demodulation.

Figure 18:
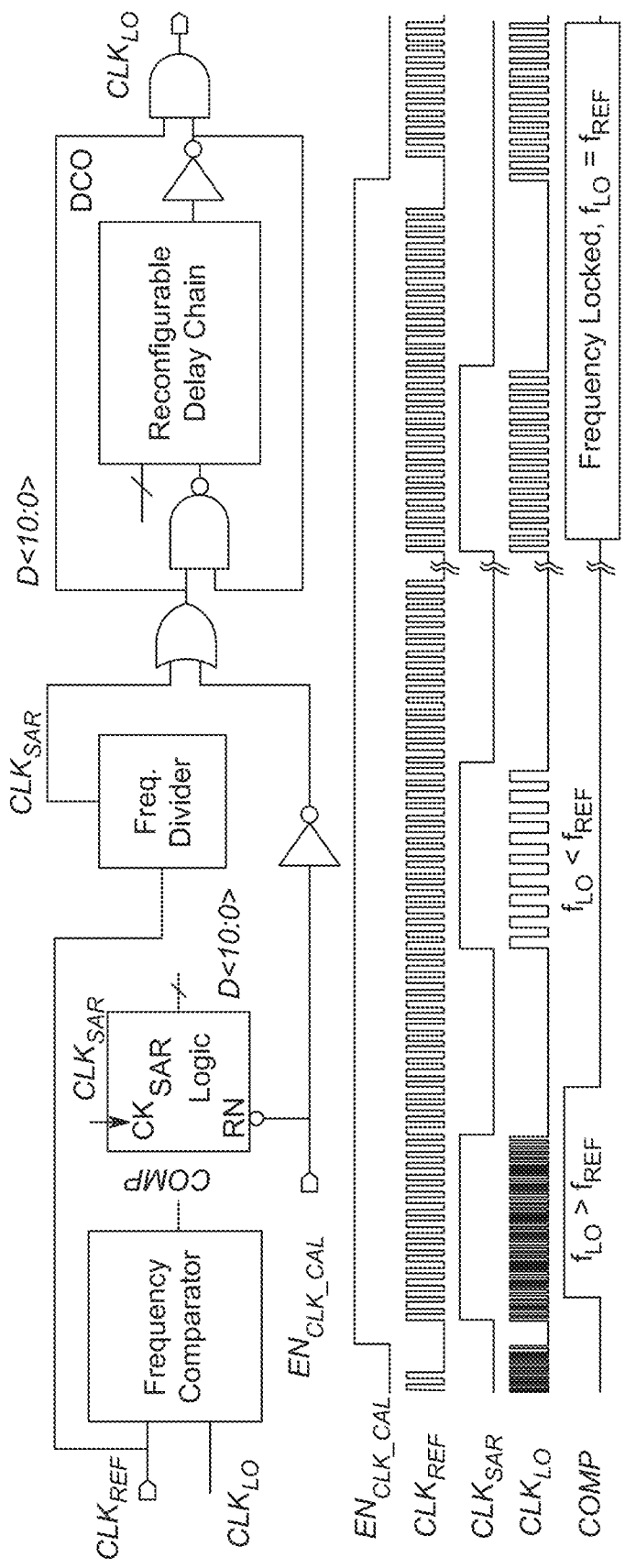
FIG. 18 illustrates schematics and operation waveforms of the frequency-locking-based local timing reference generation.

While recovering a PVT-invariant clock from the source is straightforward, it fails when the carrier field is absent and thus incompatible with the notch-based scheme. To address this, an LO in each implant is frequency locked to the clock recovered from the source ($CLK_{REF}$) as the timing reference ($CLK_{LO}$) for demodulation. The frequency locking is autonomously performed before each downlink data transfer session with SAR logic, as shown in FIG. 18.

Uplink Backscatter with FDMA (Frequency Division Multiple Access)

Figure 19:
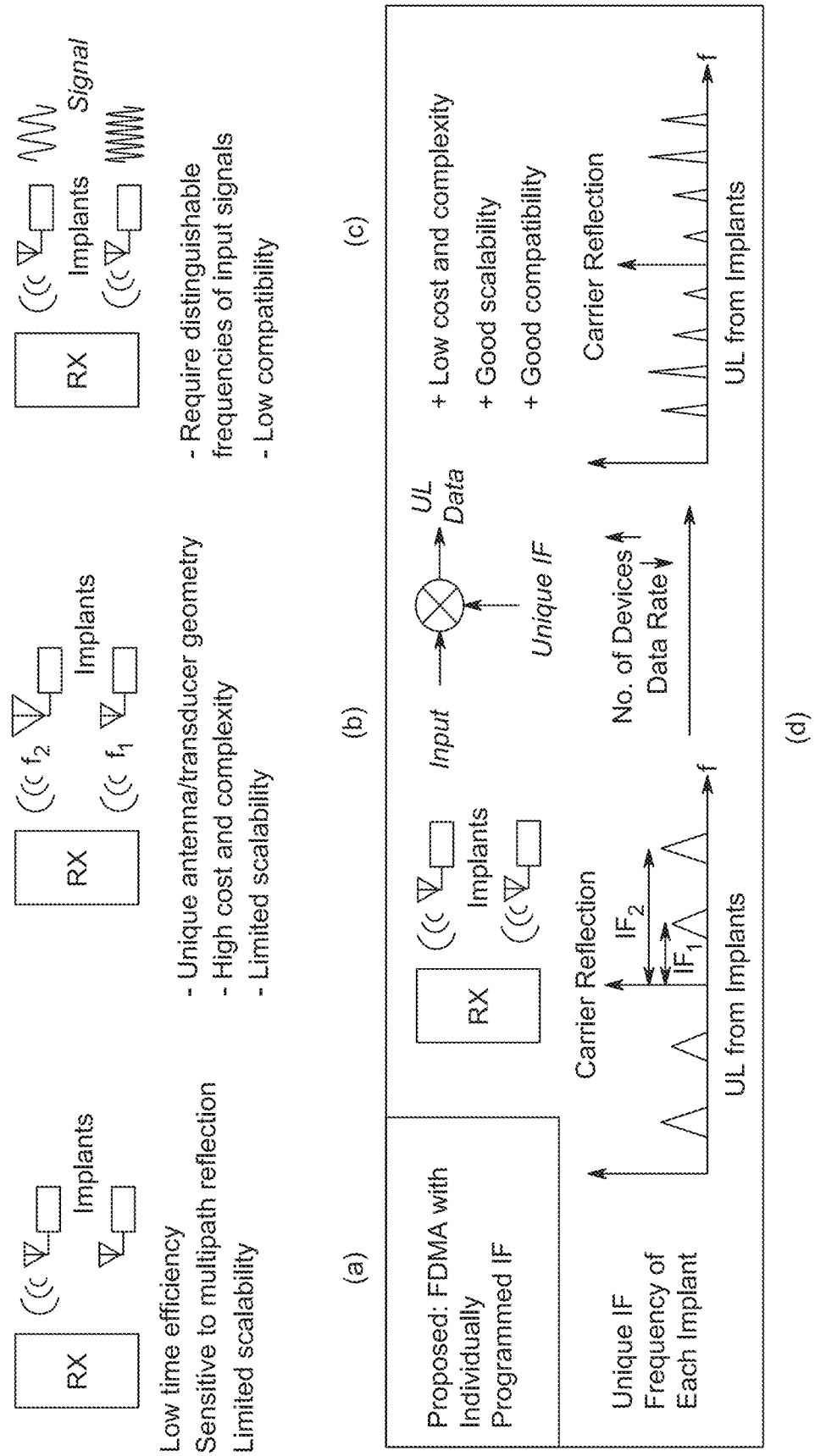
FIG. 19 illustrates existing multiple-access uplink telemetry strategies and principles of frequency division multiple access of an embodiment according to the present disclosure.

Exemplary embodiments of the present disclosure may comprise multiple implantable devices. Accessing each implantable device's feedback is important, which requires a multi-access uplink. FDMA is preferred over TDMA (Time Division Multiple Access) [3] for higher timing efficiency. However, the existing FDMA uplink for multiple implants requires different carrier frequencies [1] or input signal frequencies [2], limiting their scalability and compatibility, as shown in FIG. 19 panels (a), (b) and (c).

Figure 20:
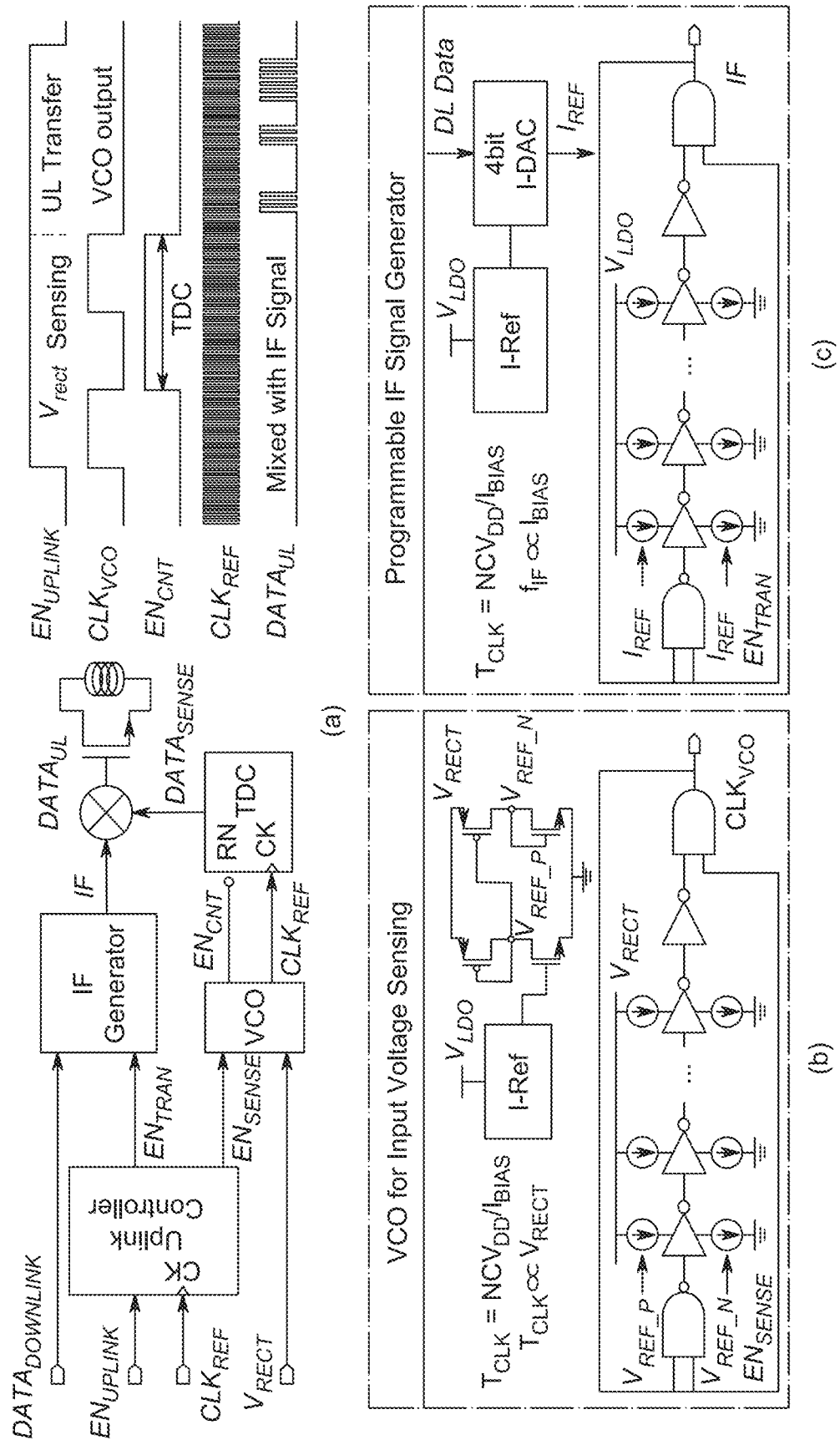
FIG. 20 illustrates schematics of an embodiment according to the present disclosure.
Figure 21:
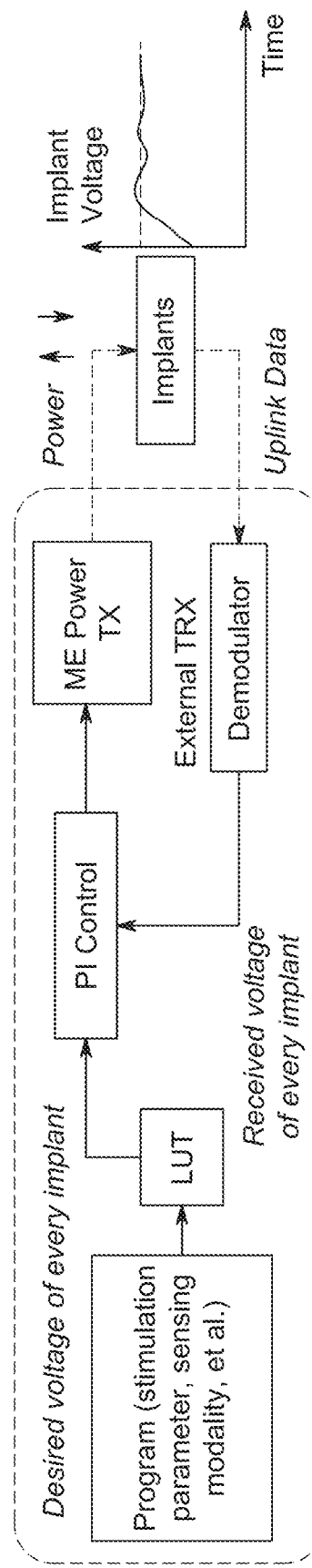
FIG. 21 illustrates a block diagram of the proposed closed-loop global power control.

Using intermediate frequency (IF) has shown benefits for SNR in inductive backscatter [14]. This work further leverages IF to realize low-cost, scalable FDMA in backscatter by mixing the individually programmed IF with the uplink data, as shown in FIG. 19 panel (d). With this mechanism, each of the implants are accessible to the external TRX simultaneously [15]. The data rate of the implants is programmed based on the channel condition to optimize the signal-noise ratio (SNR). In an exemplary embodiment, the uplink module comprises a voltage-controlled oscillator (VCO) based quantizer for implant voltage $V_{RECT}$ sensing as shown in FIG. 6 panel (a), a time-to-digital converter (TDC), a controller, and an intermediate frequency (IF) generator, which is a programmable current-starved oscillator with uniform tuning steps as shown in FIG. 20 panel (b). FIG. 21 shows a block diagram of the proposed closed-loop global power control Adaptive Global Power Transfer Control With the help of on-chip physical unclonable function (PUF) implantable devices (IDs), each implant's functionalities can be individually programmed and controlled by the external transceiver, which knows the received power of each implant though the multi-access uplink. The transceiver adapts the power transmitter's output power to regulate the implant's input power based on its real-time workload and the channel efficiency. The proposed closed-loop control of wireless power transfer can significantly mitigate power delivery fluctuations led by varying distance and misalignment and avoid unnecessary power consumption of the external transceiver under light workloads.

Measurement Results

Figure 22:
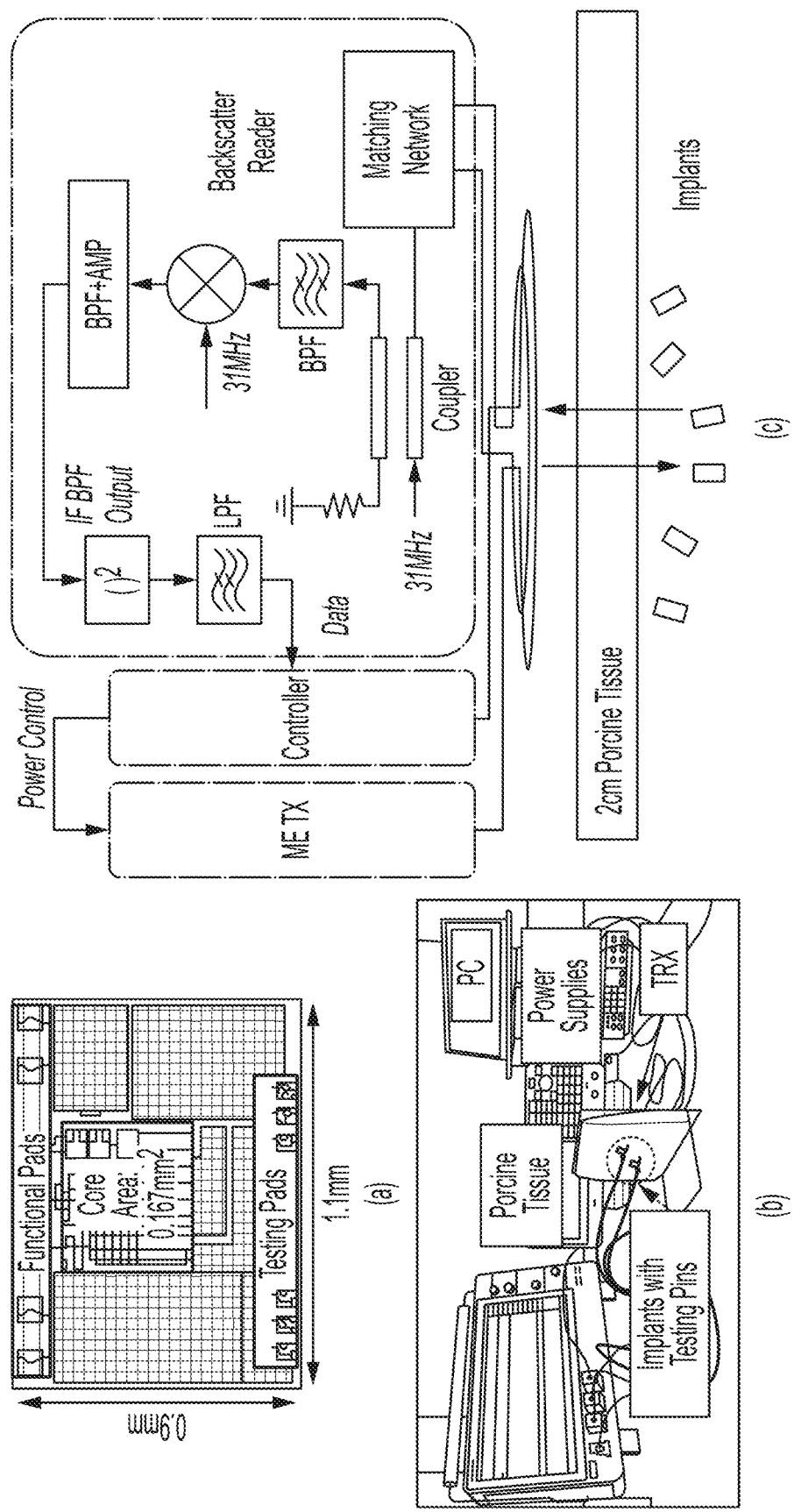
FIG. 22 illustrates an implant chip micrograph and an in-vitro test setup of an embodiment according to the present disclosure.

In one exemplary embodiment, the implant SoC is fabricated in TSMC 180-nm CMOS technology, as shown in FIG. 22 panel (a). In this example, the BioNet system is measured in vitro with a 2-cm-thick porcine tissue as shown in FIG. 22 panel (b) and (c).

Figure 23:
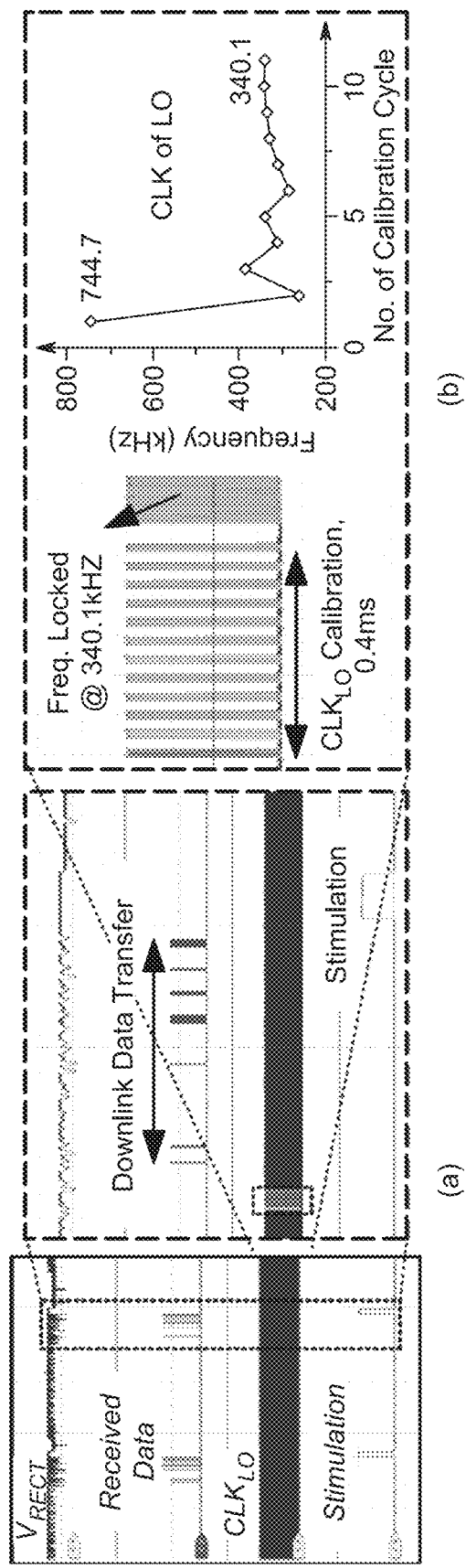
FIG. 23 illustrates waveforms of an embodiment according to the present disclosure.
Figure 24:
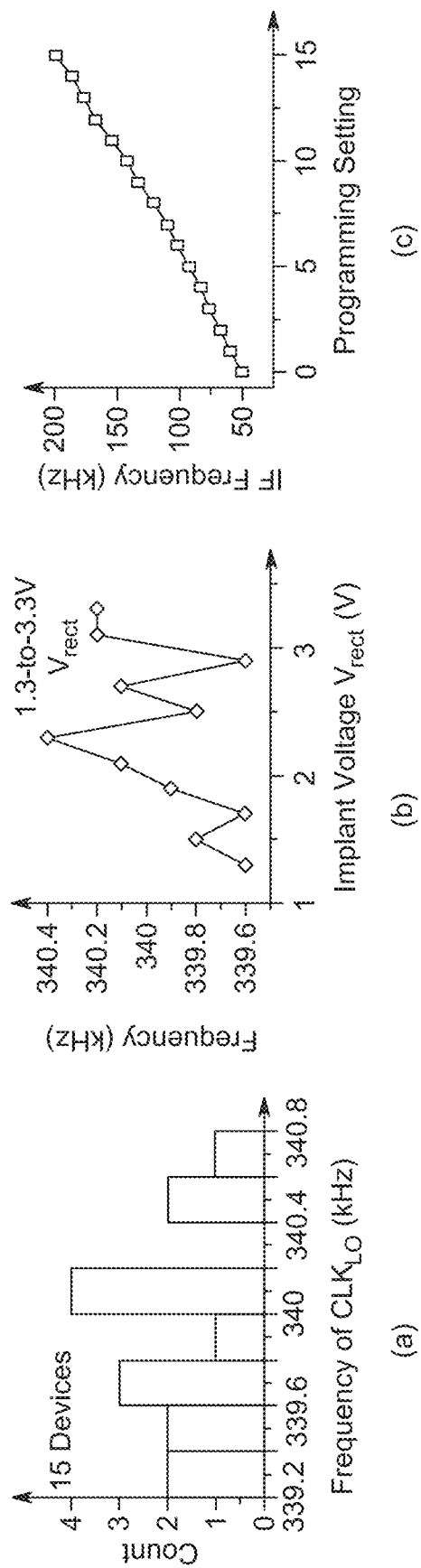
FIG. 24 illustrates measured clock $CLK_{LO}$ locking, input voltages variations; and measured frequency of an embodiment according to the present disclosure.

The implants continuously receive power during the downlink and uplink data transfer as shown in FIG. 23 panel (a). Device programming downlink data is decoded by a self-calibrated timing reference $CLK_{LO}$. The LO accurately locks to the 340.1-kHz carrier frequency in 0.4 ms, as shown in FIG. 23 panel (b). In this embodiment, the measured $CLK_{LO}$ shows 0.2% maximum error across a 2-V input voltage change in 15 devices, demonstrating its robustness to process and voltage variations, as shown in FIG. 24 panels (a), (b). For instance, the IF oscillator for data uplink can be programmed in the 50-to-200-kHz range as shown in FIG. 24 panel (c).

Figure 25:
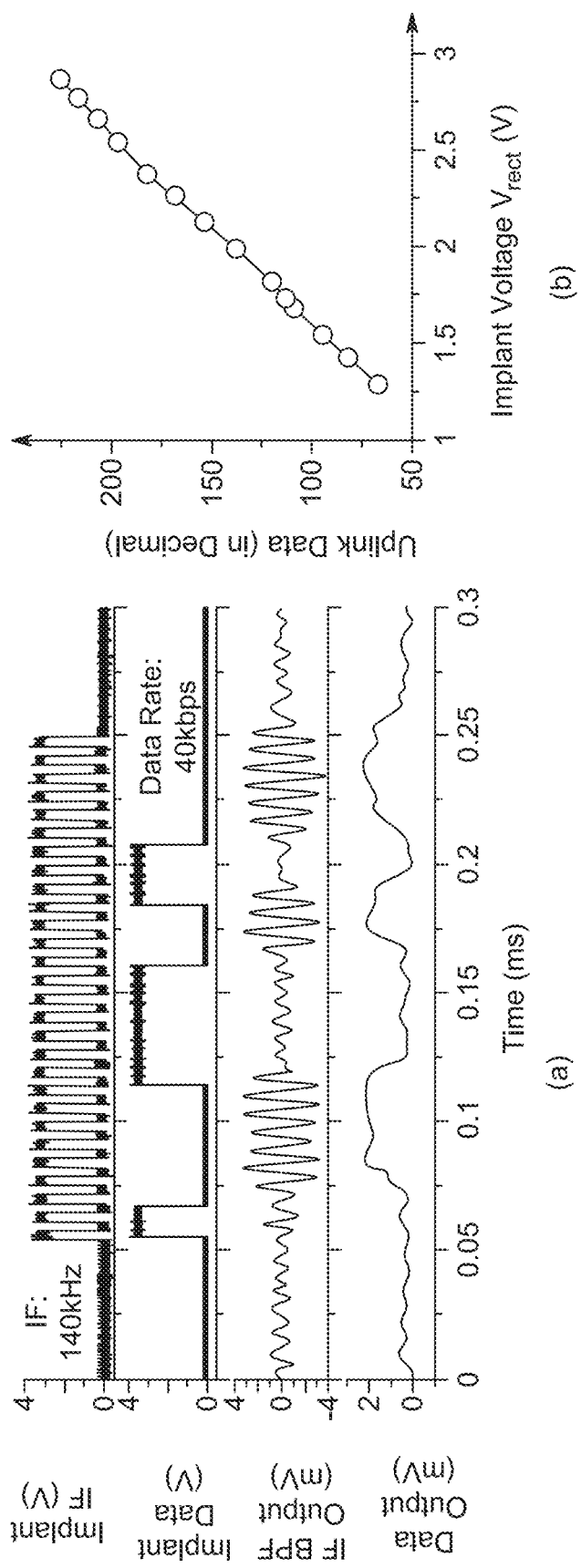
FIG. 25 illustrates measured waveforms of uplink data implant voltage feedback of an embodiment according to the present disclosure.

FIG. 25 shows the operation waveform of the uplink telemetry and the sensing and reporting of implant's received voltage. The system's uplink achieves a bit error rate (BER) of 5.5E-5 through the 2-cm porcine tissue when transmitting a 40-kbps PRBS with a 0-dBm backscatter receiver coil power (FIG. 26 (a)). Furthermore, multi-access uplink is illustrated by the spectrum of two implants transmitting data simultaneously at distinct, individually programmed IF of 83 and 108 kHz (FIG. 26 (b)).

Figure 27:
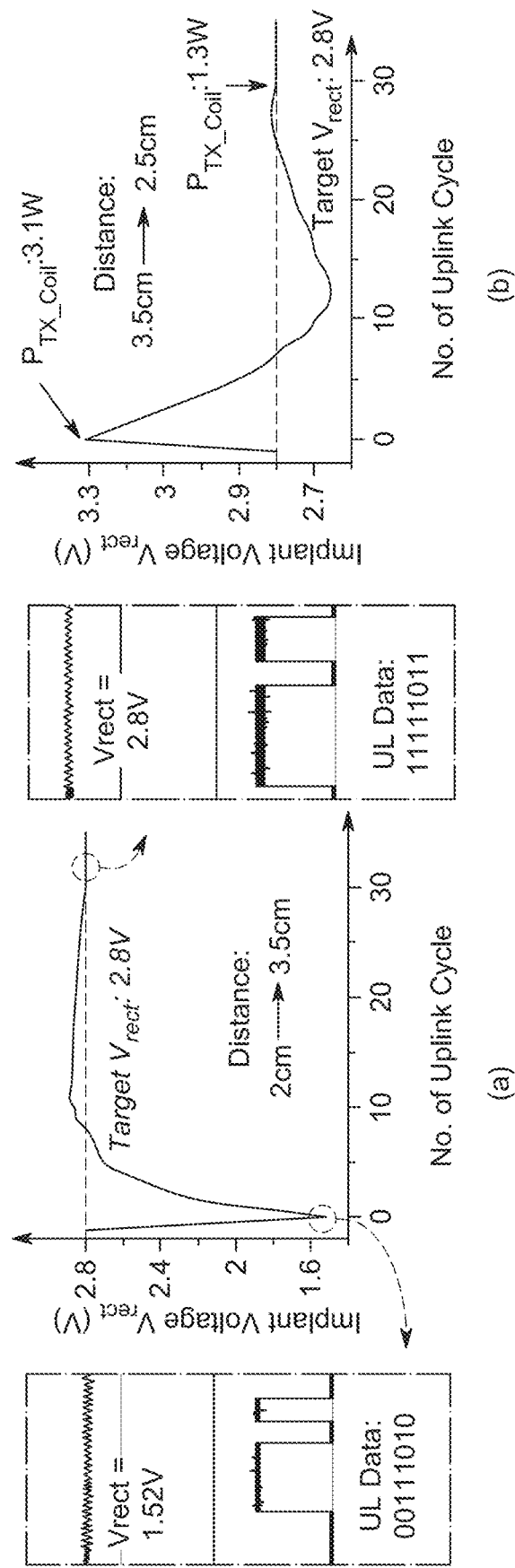
FIG. 27 illustrates measured sample operations of global wireless power transfer control against device movements for an embodiment according to the present disclosure.

FIG. 27 demonstrates the continuous closed-loop wireless power transfer regulation with changing transceiver-implant distance. With a 1.5-cm distance increase, ME voltage drops from 2.8 V to 1.52 V, resulting in a maximum 1.38-mW reduction of received power. The implant's voltage then resumes to the desired 2.8 V after 30 tuning cycles with adaptive control of the magnetoelectric transmitter's power.

Figure 28:
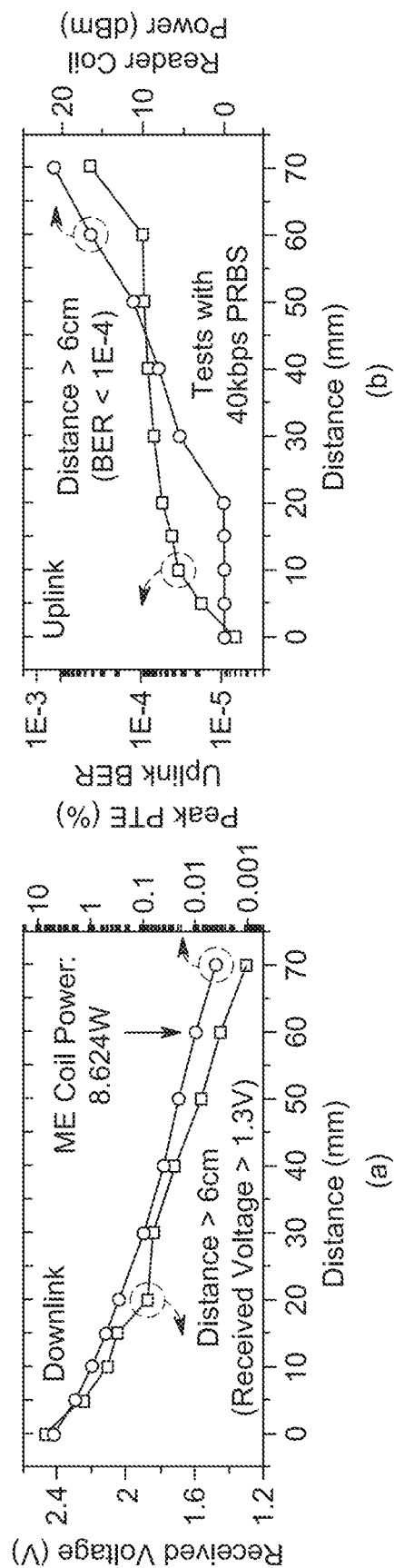
FIG. 28 illustrates measured received voltage, power transfer efficiency and uplink BER at various distances between the external TRX and the implant of an embodiment according to the present disclosure.

When the distance decreases from 3.5 cm to 2.5 cm, the regulation loop saves 1.8 W (i.e. 58%) of ME TX coil power. The implant is fully functional (i.e., receiving >1.3 V from ME WPT and achieving <1E-4 uplink BER) at 6 cm away from the TRX without violating IEEE safety limits (a maximum TX coil power of 17.6 W at 340 kHz in COMSOL) as shown in FIG. 28. In comparison with mm-sized state-of-the-art [3], [5], [11], the proposed work achieves the best PTE and the largest operating distance. Due to the time-domain modulation, its ratio of data rate/ $f_{carrier}$ in downlink is much higher than [3], [11] and comparable with [13], which operates with a much smaller distance. It enables FDMA in uplink with individually programmed IF (see FIG. 29, which includes a table showing a comparison with state-of-the-art integrated power and telemetry platforms for wireless bio-implants).

Figure 30:
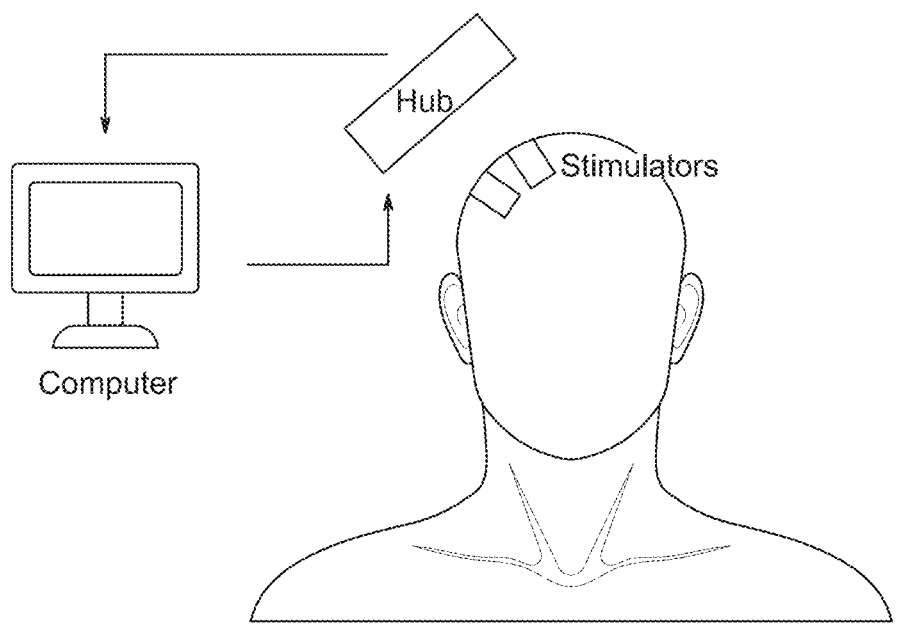
FIG. 30 illustrates a conceptual diagram of an embodiment according to the present disclosure comprising a computer processor, a hub and stimulators positioned proximal to the spine of a patient to provide neurostimulation to the brain.
Figure 31:
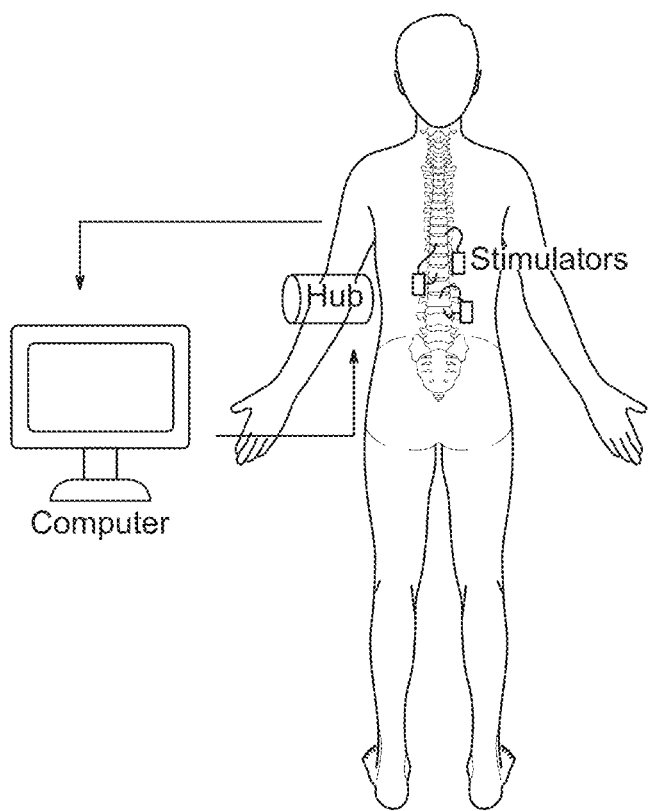
FIG. 31 illustrates a conceptual diagram of an embodiment according to the present disclosure comprising a computer processor, a hub and stimulators positioned proximal to the spine of a patient to provide neurostimulation to the spinal cord.

FIG. 30 illustrates a conceptual diagram of one embodiment of a system comprising a computer processor, a hub (e.g. external transceiver) and stimulators (e.g. magnetoelectric implants) positioned proximal to the skull and brain of a patient to provide neurostimulation to the brain (e.g. cortical stimulation). FIG. 31 illustrates a conceptual diagram of one embodiment of a system comprising a computer processor, a hub (e.g. external transceiver) and stimulators (e.g. magnetoelectric implants) positioned proximal to the spine of a patient to provide neurostimulation to the spinal cord.

Figure 32:
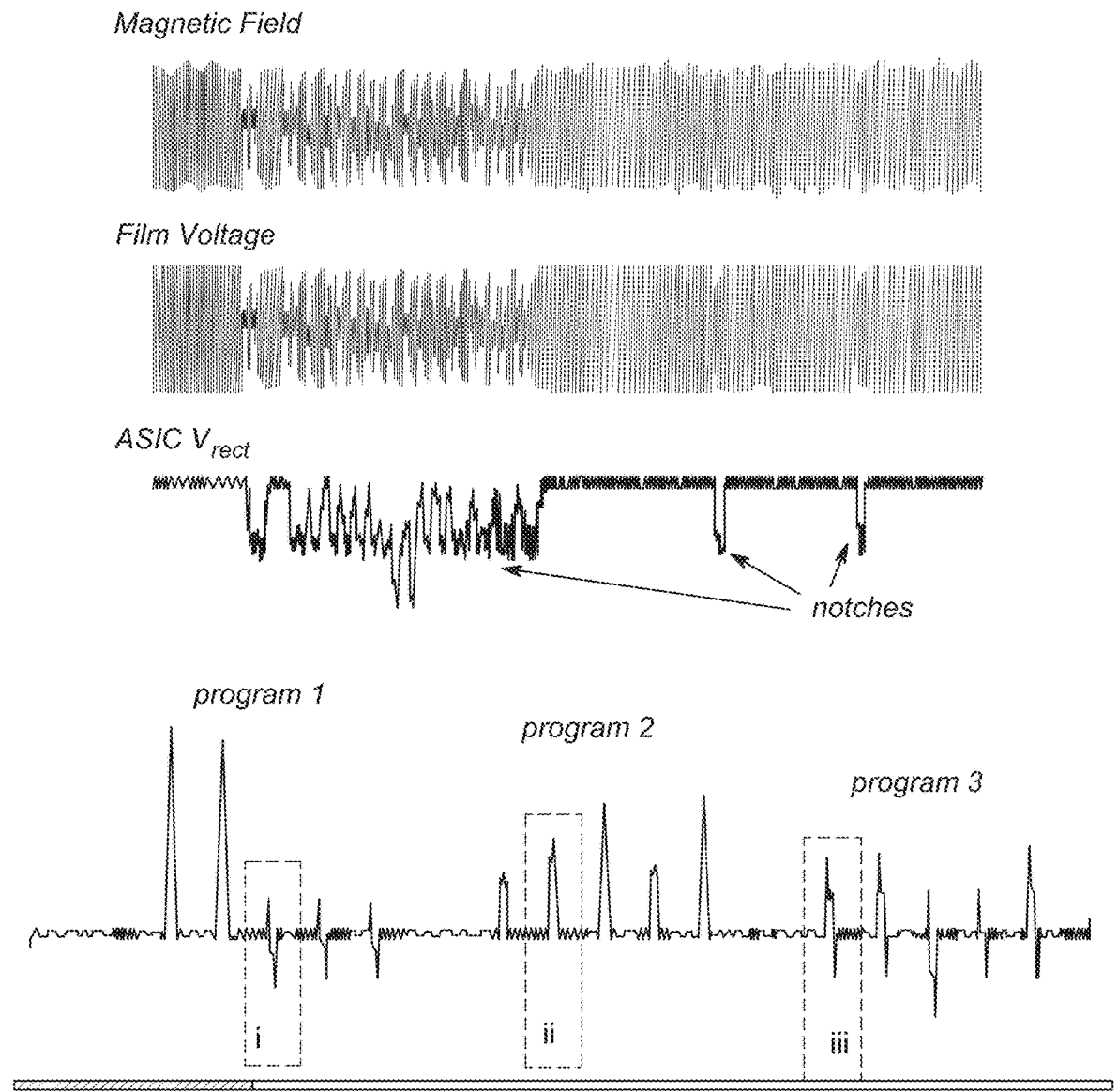
FIG. 32 illustrates data demonstrating that an embodiment according to the present disclosure can be powered by magnetoelectric film.
Figure 33:
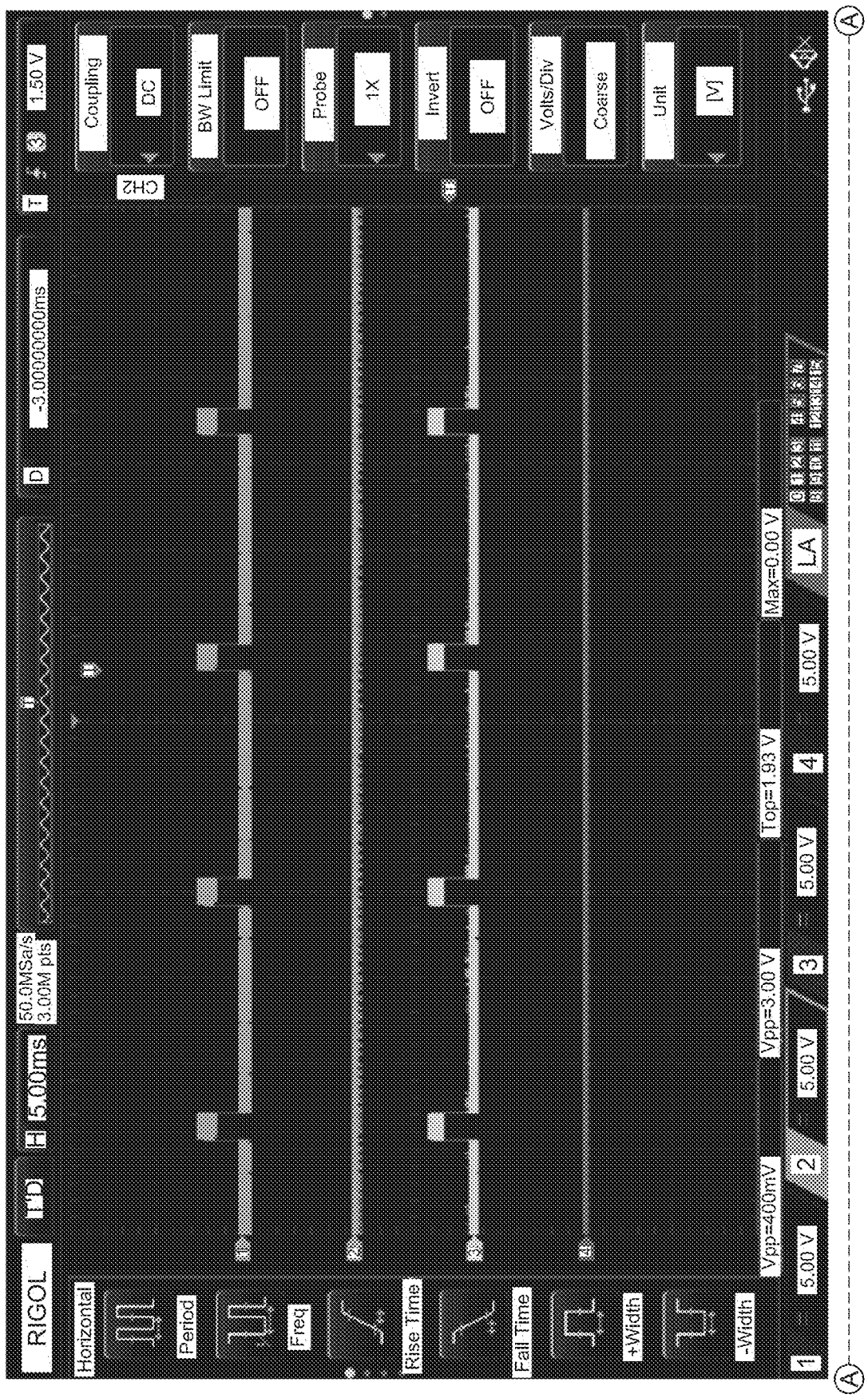
FIG. 33 illustrates data showing that multiple embodiments according to the present disclosure can be programmed at once.
Figure 33:
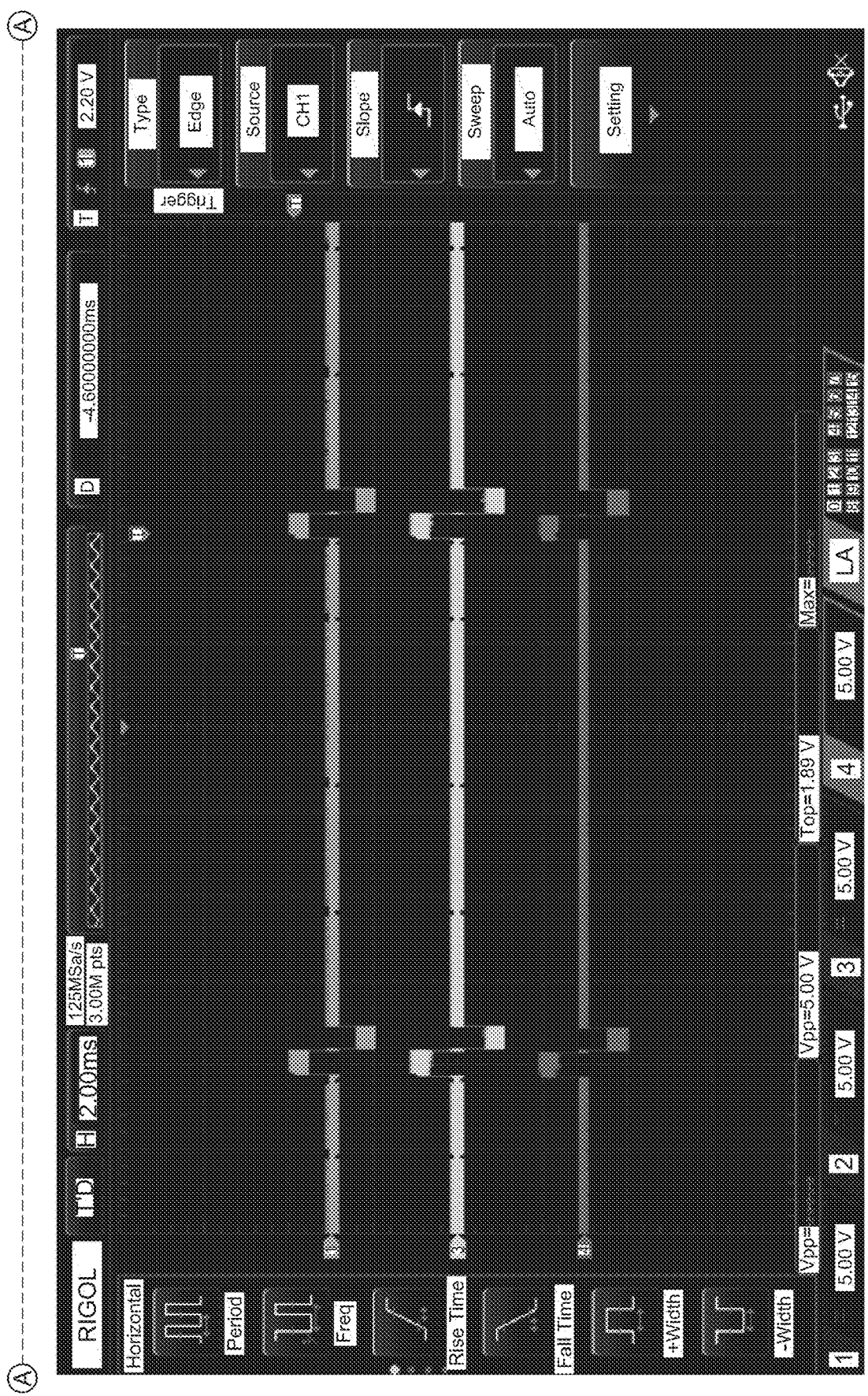

FIG. 32 illustrates data demonstrating that the device can be powered by magnetoelectric film, while FIG. 33 illustrates data showing that multiple devices can be programmed at once.

Figure 34:
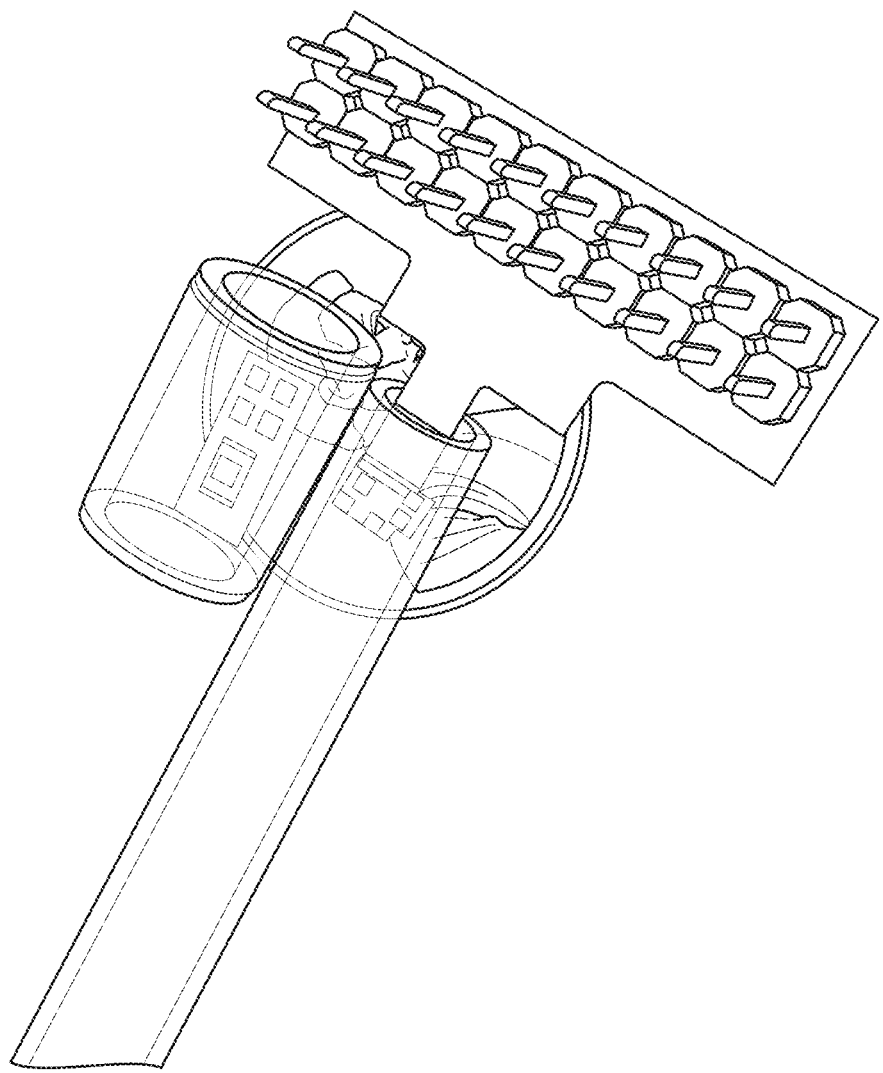
FIG. 34 illustrates an image of an embodiment according to the present disclosure showing a glass device without leads for cortical stimulation.

FIG. 34 provides an image showing a glass device without leads for cortical stimulation. In one embodiment, custom through glass via (TGV) wafers are obtained and platinum and titanium are deposited and patterned to create electrode contacts on TGV wafer. In particular embodiments, a laser is used to cut individual "caps" from TGV wafer, and ASIC is bonded to a custom flex-rigid or rigid PCB. ME film is connected to PCB with wire and conductive silver epoxy. In specific embodiments, the custom PCB is bonded to inside of cap with conductive silver epoxy, and the cap is sealed to glass tube with medical grade epoxy or laser welding, and an identical sized cap is bonded to top of glass tube.

Figure 36:
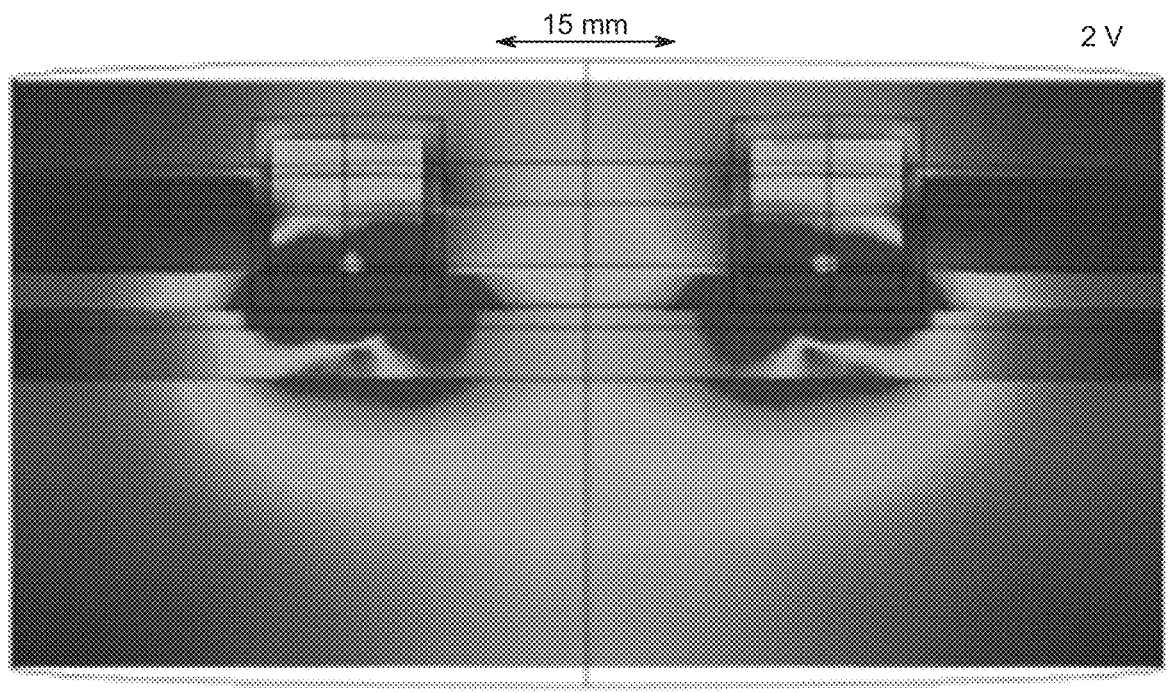
FIG. 36 illustrates coordinated stimulation between two glass motes of an embodiment according to the present disclosure.
Figure 37:
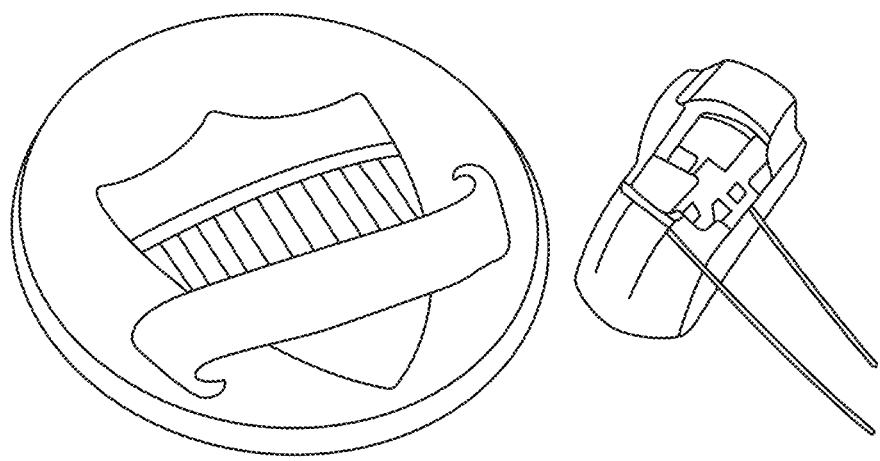
FIG. 37 illustrates an image of an embodiment according to the present disclosure showing an epoxy encapsulated device with leads for spinal stimulation.
Figure 38:
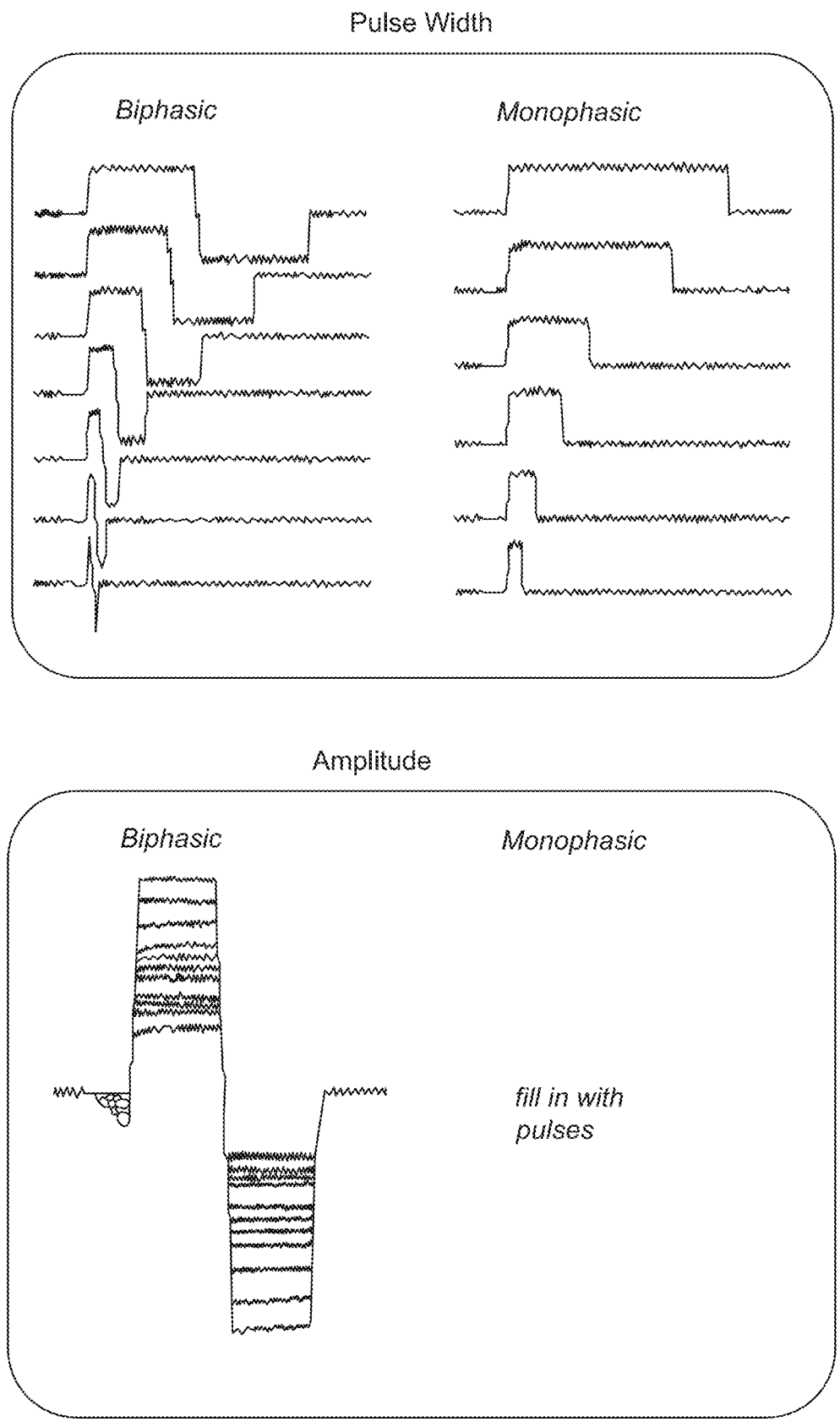
FIG. 38 illustrates data showing that stimulation is digitally programmable with ASIC according to an embodiment according to the present disclosure.

FIG. 35 illustrates alternative options for glass packaging design and electrode spacing in particular embodiments. FIG. 36 illustrates simulation of coordinated stimulation between two glass motes, while FIG. 37 provides an image of an embodiment showing an epoxy encapsulated device with leads for spinal stimulation. In this embodiment, ASIC is bonded to custom PCB, and the ME film is connected to PCB with wire and conductive silver epoxy. Stimulation leads are also connected to PCB with silver epoxy, and the package is 3D printed with a cavity for the ME film. The ME film is sealed inside box and PCB is sealed to outside of box with medical grade clear epoxy. FIG. 38 illustrates data showing that stimulation is digitally programmable with ASIC.

Figure 39:
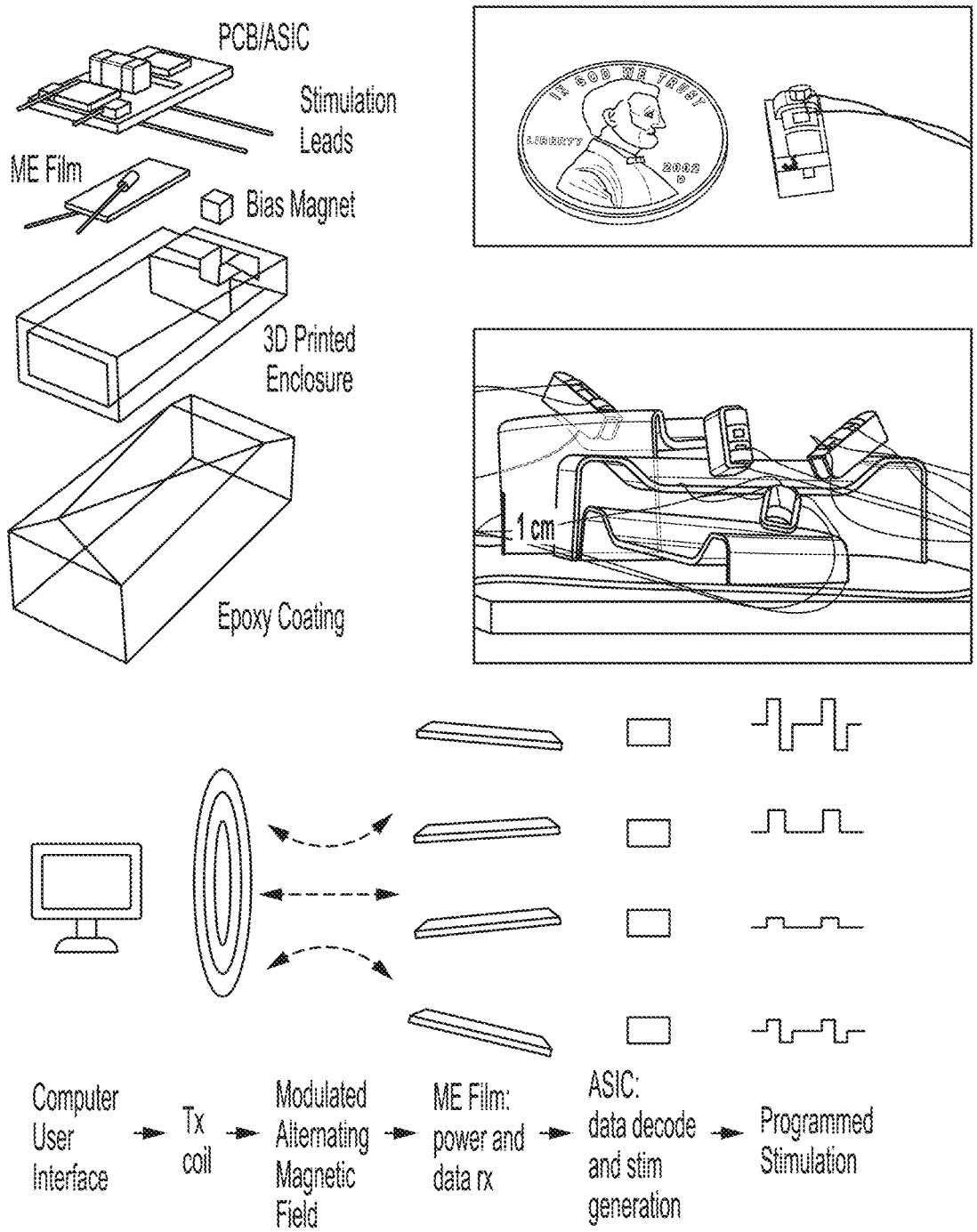
FIG. 39 illustrates an embodiment of a battery-free, wireless, stimulation implant according to the present disclosure.

FIG. 39 shows an embodiment of a battery-free, wireless, stimulation implant according to the present disclosure. Aspects include a computer user interface, transmitter coil, modulated alternating magnetic field, ME film (power and data receiver), ASIC (data decode and stimulation generation, and programmed stimulation.

Figure 41:
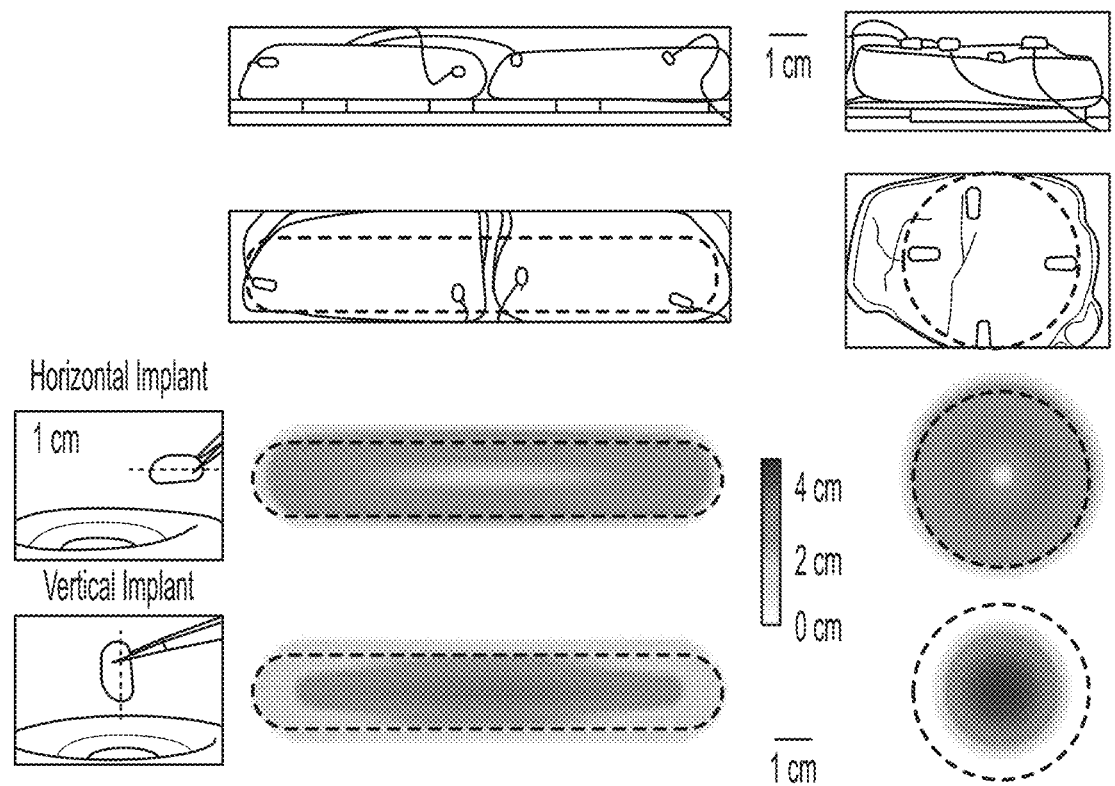
FIG. 41 illustrates that implant placement and coil geometry are both reconfigurable including horizontal or vertical configurations.
Figure 43:
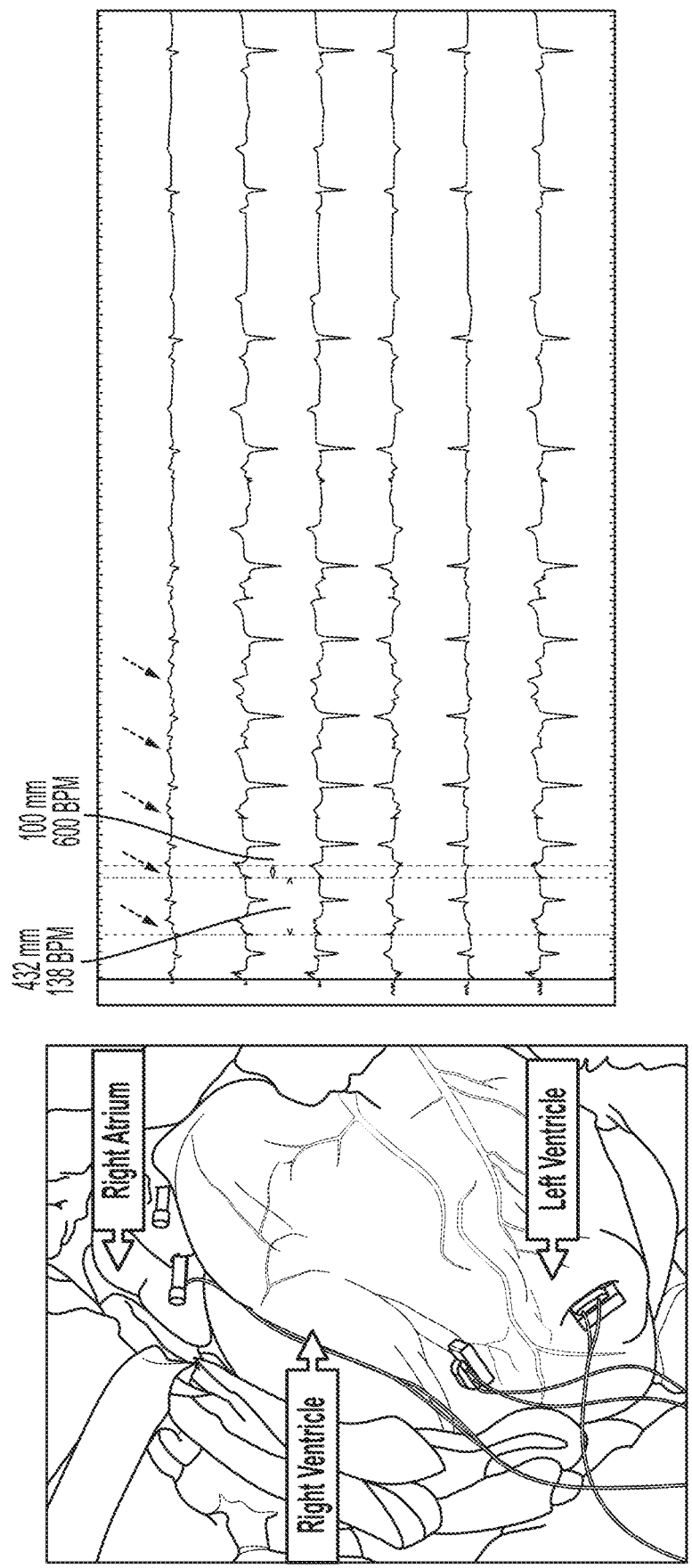
FIG. 43 illustrates an embodiment of the present disclosure implemented as a pacemaker.

FIG. 40 shows operational aspects of a network of four individually addressable implants. FIG. 41 illustrates that implant placement and coil geometry are both reconfigurable, including for example horizontal or vertical configurations. FIG. 42 shows an embodiment implemented for stimulation of a rat spinal cord, while FIG. 43 illustrates an embodiment implemented as a pacemaker.

In summary, exemplary embodiments of the present disclosure include a wireless network of mm-sized biomedical implants exploiting adaptive closed-loop control of ME power transfer and novel schemes for multi-access bidirectional communications. In particular embodiments, the adopted global WPT control significantly improves the robustness against perturbations of distance and alignment and the system's overall efficiency. In specific embodiments, the time-domain modulated downlink works simultaneously with the power transfer, and can achieve a 5% peak power transfer efficiency and a 62.3-kbps maximum data rate. FDMA uplink is realized by individually programmed IF with a maximum data rate of 40 kbps. Exemplary embodiments have been tested in vitro and have demonstrated a >6-cm working distance between the external transceiver and the implant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

[1] A. Khalifa et al., "The Microbead: A Highly Miniaturized Wirelessly Powered Implantable Neural Stimulating System," TBioCAS, June 2018.

[2] M. M. Ghanbari et al., "A Sub-mm3 Ultrasonic Free-Floating Implant for Multi-Mote Neural Recording," JSSC, November 2019.

[3] V. W. Leung et al., "Distributed Microscale Brain Implants with Wireless Power Transfer and Mbps Bi-directional Networked Communications," in CICC, April 2019.

[4] Z. Yu et al., "Multisite bio-stimulating implants magnetoelectrically powered and individually programmed by a single transmitter," in CICC, April 2021.

[5] D. K. Piech et al., "A wireless millimetre-scale implantable neural stimulator with ultrasonically powered bidirectional communication," Nat. Biomed. Eng., February 2020.

[6] Y. Jia et al., "A mm-sized free-floating wirelessly powered implantable optical stimulating system-on-a-chip," in ISSCC, February 2018.

[7] J. Pan et al., "An inductively-coupled wireless power-transfer system that is immune to distance and load variations," in ISSCC, February 2017.

[8] X. Li et al., "A 13.56 MHz Wireless Power Transfer System With Reconfigurable Resonant Regulating Rectifier and Wireless Power Control for Implantable Medical Devices," JSSC, April 2015.

[9] J. Tang et al., "A Wireless Power Transfer System with Up-to-20% Light-Load Efficiency Enhancement and Instant Dynamic Response by Fully Integrated Wireless Hysteretic Control for Bioimplants," in ISSCC, February 2021.

[10] Z. Yu et al., "MagNI. A Magnetoelectrically Powered and Controlled Wireless Neurostimulating Implant," TBioCAS, December 2020.

[11] J. Thimot et al., "A 27-Mbps, 0.08-mm3 CMOS Transceiver with Simultaneous Near-field Power Transmission and Data Telemetry for Implantable Systems," in CICC, March 2020.

[12] J. Lim et al., "A Light Tolerant Neural Recording IC for Near-Infrared-Powered Free Floating Motes," in VLSI, June 2021.

[13] Y. Park et al., "A Frequency-Splitting-Based Wireless Power and Data Transfer IC for Neural Prostheses with Simultaneous 115 mW Power and 2.5 Mb/s Forward Data Delivery," in ISSCC, February 2021.

[14] N.-C. Kuo et al., "Inductive Wireless Power Transfer and Uplink Design for a CMOS Tag With 0.01 mm2 Coil Size," Microw. Wirel. Compon. Lett., October 2016.

[15] D. Yeager, W. Biederman, N. Narevsky, E. Alon, and J. Rabaey, "A fully-integrated 10.5 W miniaturized (0.125 mm2) wireless neural sensor," in Symposium on VLSI Circuits, June 2012.

Singer, A., S. Dutta, E. Lewis, Z. Chen, J. C. Chen, N. Verma, B. Avants, A. K. Feldman, J. O'Malley, M. Beierlein, C. Kemere, and J. T. Robinson, Magnetoelectric Materials for Miniature, Wireless Neural Stimulation at Therapeutic Frequencies. Neuron, 2020.

Z. Yu, J. C. Chen, F. T. Alrashdan, B. W. Avants, Y. He, A. Singer, J. T. Robinson, and K. Yang, "MagNI. A Magnetoelectrically Powered and Controlled Wireless Neurostimulating Implant," IEEE Transactions on Biomedical Circuits and Systems, pp. 1-1, 2020. Conference Name: IEEE Transactions on Biomedical Circuits and Systems.

Zhu, Dibin. Methods of frequency tuning vibration based micro-generator. Diss. University of Southampton, 2009.

What is claimed:

1. A wireless bioelectronic system, comprising:
an external transceiver; and
a plurality of implantable devices, wherein:
   each implantable device comprises an electrical circuit and a magnetoelectric film that is coupled to the electrical circuit,
   the external transceiver is configured to simultaneously transmit a magnetic field for wireless transmission of power to each of the plurality of implantable devices,
   the magnetoelectric film is configured to generate backscattered signal in response to the magnetic field transmitted by the external transceiver,
   each of the plurality of implantable devices is configured to transmit an uplink communication, using the backscattered signal, to the external transceiver after the magnetic field is transmitted from the external transceiver,
   the uplink communication includes workload corresponding to each of the plurality of implantable devices, and
   the external transceiver is configured to dynamically adjust, based on the workload corresponding to each of the plurality of implantable devices, the power transmitted to each of the plurality of implantable devices.

2. The wireless bioelectronic system of claim 1, wherein each of the plurality of implantable devices is configured to stimulate and/or record electrophysiological activity.

3. The wireless bioelectronic system of claim 1, wherein the backscattered signal is generated by each of the plurality of implantable devices oscillating at a resonant frequency of the implantable device.

4. The wireless bioelectronic system of claim 1, wherein the electrical circuit is configured to modulate a resonant frequency of the magnetoelectric film by applying different electric loading conditions that change a property of the magnetoelectric film.

5. The wireless bioelectronic system of claim 1, wherein the transceiver comprises a magnetoelectric transmitter, a controller and a receiver.

6. The wireless bioelectronic system of claim 5, wherein the external transceiver includes an inductive coil electrode or ultrasonic transducer.

7. The wireless bioelectronic system of claim 1, wherein the plurality of implantable devices are configured to be implanted along a spinal column.

8. The wireless bioelectronic system of claim 1, wherein the uplink communication from each of the plurality of implantable devices comprises data.

9. The wireless bioelectronic system of claim 8, wherein the data is transmitted with a modulated magnetic field, near field communication (NFC), light, or bluetooth low energy.

10. The wireless bioelectronic system of claim 8, wherein the data contains received power.

11. The wireless bioelectronic system of claim 8, wherein the data contains biomarkers.

12. The wireless bioelectronic system of claim 11, wherein biomarkers include local field potential, spectrograms of the local field potential, or power in specific frequency bands such as theta band power, alpha band power, or spiking band power.

13. The wireless bioelectronic system of claim 1, wherein nerve stimulation is conditioned based on data received from the plurality of implantable devices.

14. The wireless bioelectronic system of claim 1, wherein the plurality of implantable devices are implanted in or above left and/or right dorsolateral prefrontal cortex.

15. The wireless bioelectronic system of claim 1, wherein the plurality of implantable devices is implanted in or above a spinal cord.

16. A method of stimulating neural tissue, the method comprising:
   generating a magnetic field within an external base station, wherein the external base station includes a transceiver;
   simultaneously transmitting, from the transceiver, the magnetic field to each of a plurality of implantable devices for wireless transmission of power, wherein each implantable device of the plurality of implantable devices comprises:
      an electrical circuit coupled to a magnetoelectric film,
   the magnetoelectric film is configured to generate backscattered signal in response to the magnetic field transmitted by the transceiver,
   each of the plurality of implantable devices are configured to transmit an uplink communication, using the backscattered signal, to the transceiver after the magnetic field is transmitted from the transceiver,
   the uplink communication includes workload corresponding to each of the plurality of implantable devices, and
   the transceiver is configured to dynamically adjust, based on the workload corresponding to each of the plurality of implantable devices, the power transmitted to each of the plurality of implantable devices.

17. The method of claim 16, further comprising:
producing an electrical output signal using the magnetoelectric film; and
modifying the electrical output signal using the electrical circuit.

18. The method of claim 16, wherein the transceiver comprises a magnetoelectric transmitter, a controller and a receiver.

19. The method of claim 18, wherein the receiver includes an inductive coil electrode, or ultrasonic transducer.

* * * * *